(12) United States Patent
Vetter et al.

(10) Patent No.: US 10,117,508 B2
(45) Date of Patent: *Nov. 6, 2018

(54) FASTENABLE DEVICE FOR ORAL CAVITY POSITION DETECTION

(71) Applicant: Braun GmbH, Kronberg (DE)

(72) Inventors: Ingo Vetter, Karben (DE); Frank Kressmann, Eschborn (DE); Alexandre Halbach, Battice (BE)

(73) Assignee: The Procter & Gamble Company, Cincinnati, OH (US)

( * ) Notice: Subject to any disclaimer, the term of this patent is extended or adjusted under 35 U.S.C. 154(b) by 470 days.

This patent is subject to a terminal disclaimer.

(21) Appl. No.: 14/806,553

(22) Filed: Jul. 22, 2015

(65) Prior Publication Data

US 2016/0022024 A1    Jan. 28, 2016

(30) Foreign Application Priority Data

Jul. 22, 2014   (EP) ..................... 14178045

(51) Int. Cl.
*A46B 15/00* (2006.01)
*G01D 5/14* (2006.01)
(Continued)

(52) U.S. Cl.
CPC ...... *A46B 15/0006* (2013.01); *A46B 15/0008* (2013.01); *A46B 15/0014* (2013.01);
(Continued)

(58) Field of Classification Search
CPC ............ A46B 15/0081; A46B 15/0008; A46B 15/0071; A46B 15/0014; A46B 15/0006;
(Continued)

(56) References Cited

U.S. PATENT DOCUMENTS 6,536,068 B1    3/2003   Yang et al.
6,689,078 B1 *  2/2004   Rehkemper ............ A61C 17/30
                                                    15/29
(Continued)

FOREIGN PATENT DOCUMENTS

AU      2013101537 A4    12/2013
DE     102008027317 A1   12/2009
(Continued)

OTHER PUBLICATIONS

Masaharu, "Attachment for Inter-tooth Cleaner", JP 9215701 (English Machine Translation, Published Aug. 19, 1997).*
U.S. Appl. No. 14/806,527, filed Jul. 22, 2015, Ingo Vetter et al.

*Primary Examiner* — Farhana Hoque
(74) *Attorney, Agent, or Firm* — Parker D. McCrary; Vladimir Vitenberg

(57) ABSTRACT

A fastenable device includes a housing having a base portion, a head portion opposite to the base portion, and a body portion between the base portion and the head portion. The base portion has a first fastener in the form of a full ring integral to the housing and defining a through-hole. The head portion has a second fastener in the form of an open ring integral to the housing and defining a snappable recess. The device includes a frequency generator housed in the housing and electrically connected to an electrode pair disposed on the housing, for applying a voltage with at least two different frequencies between the electrodes.

13 Claims, 10 Drawing Sheets

(51) Int. Cl.
  *A61C 15/02* (2006.01)
  *A61C 15/04* (2006.01)
  *A61C 17/02* (2006.01)
  *A61C 17/22* (2006.01)
  *A61B 5/06* (2006.01)
  *A61B 17/24* (2006.01)
  *A61B 5/00* (2006.01)

(52) U.S. Cl.
  CPC ...... *A46B 15/0038* (2013.01); *A46B 15/0071* (2013.01); *A46B 15/0081* (2013.01); *A61B 5/068* (2013.01); *A61B 5/682* (2013.01); *G01D 5/14* (2013.01); *A46B 2200/108* (2013.01); *A46B 2200/1066* (2013.01); *A61B 5/002* (2013.01); *A61B 5/067* (2013.01); *A61B 5/743* (2013.01); *A61B 17/24* (2013.01); *A61C 15/02* (2013.01); *A61C 15/04* (2013.01); *A61C 17/02* (2013.01); *A61C 17/22* (2013.01)

(58) Field of Classification Search
  CPC ..... A46B 15/0038; A61B 5/068; A61B 5/682; A61B 15/0038; A61B 5/743; A61B 5/002; A61B 17/24; A61B 5/067; G01D 5/14; A61C 17/22; A61C 17/02; A61C 15/04
  USPC ............................................ 324/707; 604/20
  See application file for complete search history.

(56) References Cited

U.S. PATENT DOCUMENTS

| | | | |
|---|---|---|---|
| 7,890,193 | B2 | 2/2011 | Tingey |
| 7,917,203 | B2 | 3/2011 | Brown et al. |
| 8,175,840 | B2 | 5/2012 | Hwang |
| 8,176,591 | B2 | 5/2012 | Iwahori et al. |
| 8,341,791 | B2 | 1/2013 | Iwahori |
| 8,393,037 | B2 | 3/2013 | Iwahori et al. |
| 2003/0004431 | A1 | 1/2003 | Pinyayev |
| 2004/0194541 | A1 | 10/2004 | Sherman et al. |
| 2008/0109973 | A1 | 5/2008 | Farrell et al. |
| 2011/0010875 | A1 | 1/2011 | Iwahori et al. |
| 2012/0246858 | A1 | 10/2012 | De Vries et al. |
| 2012/0266397 | A1 | 10/2012 | Iwahori |
| 2012/0310593 | A1 | 12/2012 | Bates et al. |
| 2013/0072851 | A1* | 3/2013 | Doll .................. A61N 1/32 604/20 |
| 2014/0199651 | A1 | 7/2014 | Adachi |
| 2014/0246049 | A1 | 9/2014 | Ikkink et al. |
| 2015/0230593 | A1* | 8/2015 | Doll .................. A46B 15/0006 702/19 |

FOREIGN PATENT DOCUMENTS

| | | | |
|---|---|---|---|
| JP | 9215701 A | * | 8/1997 |
| WO | WO2007032015 A2 | | 3/2007 |

* cited by examiner

FASTENABLE DEVICE FOR ORAL CAVITY POSITION DETECTION

FIELD OF THE INVENTION

The present invention is directed to detecting oral cavity positions of an oral care implement during use by a fastenable device fastened to the implement.

BACKGROUND OF THE INVENTION

Maintaining good oral hygiene is important for oral health and even overall well-being. Proper and regular tooth brushing is a basic and important part of an oral care regimen. Various toothbrushes, including manual toothbrushes and electric toothbrushes, have been developed to facilitate effective tooth brushing. Researchers have continuously tried to improve the brushing quality, for example, by optimizing the brushing head, increasing the head rotation frequency, designing new cleaning techniques such as by way of ultrasound. Although some of these attempts have been successful in theory and even endorsed by dentists, high brushing quality has not been achieved in practice by many consumers. There are several explanations proposed. For example, at least one study reports that an adult brushes on average for 46 seconds while the recommended brushing time is generally accepted as 2 minutes. Studies even show that during this short brushing time consumers tend to brush unevenly, neglecting certain teeth surfaces and over-brushing others. This possibly leads to cavity formation and/or plaque accumulation in those surfaces where there is not enough brushing, and receding gums where there is too much brushing. Therefore, it is important for the consumer to receive real-time feedback on the brushing position and time, to optimize their brushing procedure. Such feedback relies on the ability to precisely and accurately detect the position of the toothbrush in the mouth.

There have been efforts in developing position detection technology for about a decade. For example, AU 2013 101 537 A4 (2013-12-19) discloses a toothbrush and a detachable intra-oral camera attachment externally coupled to the toothbrush. In another example, US 2012/266397 A1 (2012 Oct. 25) discloses an electric toothbrush estimating a brushing area by measuring the impedance between two electrodes by means of an impedance measuring unit. However, to date no one has broadly and cost effectively commercialized this technology. There continues to be a need of providing non-intrusive, precise and/or accurate position detection at a low cost. Position detection technology will help users improve their brushing procedure so as to mitigate the occurrence of plaque and caries, as well as gum recession. There is also a need to provide the position technology that can be fastenable to oral care implements so that the technology can be provided to those implements that otherwise would not have such position detection benefits.

SUMMARY OF THE INVENTION

The present invention attempts to address one or more of these needs.

One advantage of the present invention is providing a fastener device that is releasably fastenable to the oral care implement. The fastener device may be unfastened and re-fastened each time, for example, toothbrush bristles are replaced or even the toothbrush itself is replaced. The invention provides valuable oral area position detection to the user for every brushing episode but yet saves the user money by not subjecting the user to replacement costs every time bristles and/or toothbrush are replaced.

Another advantage of the device is the ease and simplicity of fastening, unfastening, and re-fastening the device to an oral care implement.

Another advantage of the present invention is increased accuracy of detecting a defined oral care area (e.g., as a saliva area, a cheek area or a tongue area) by applying a voltage with at least two different frequencies between the electrode pair. This is a relatively simple and cost effective way of increasing position detection accuracy. Several aspects of the invention are described.

Another aspect of the invention provides for a fastenable device comprising: a housing defined by a base portion and an opposing head portion and a body portion in between the base portion and the head portion, wherein the base portion comprises a first fastener in the form of a full ring integral to the housing defining a through-hole, and wherein the head portion further comprises a second fastener in the form of an open ring integral to the housing defining a snappable recess;

wherein the fastenable device is characterized by further comprising a frequency generator housed in the housing and is electrically connected to an electrode pair disposed on the housing, for applying a voltage with at least two different frequencies between the electrode pair.

Another aspect provides for a method of fastening a fastenable device to a toothbrush neck comprising the steps: (a) providing the fastenable device of the present invention; (b) providing a toothbrush comprises a handle portion and an opposing bristle head, with the neck portion therein between; (c) sliding the toothbrush bristle head through the through-hole of the first fastener and continuing until the handle portion abuts the first fastener; (d) squeezing the head portion or the body portion and the toothbrush neck portion together until the snappable recess snaps around at least a portion of the toothbrush neck thereby fastening the fastenable device to the toothbrush neck.

Another aspect of the invention provides for a fastenable device comprising: a housing defined by a base portion and an opposing head portion and a body portion in between the base portion and the head portion, wherein the base portion comprises a first fastener in the form of a a first open ring integral to the housing defining a first snappable recess, and wherein the head portion further comprises a second fastener in the form of a second open ring integral to the housing defining a second snappable recess;

wherein the fastenable device is characterized by further comprising a frequency generator housed in the housing and is electrically connected to an electrode pair disposed on the housing, for applying a voltage with at least two different frequencies between the electrode pair.

Another aspect of the invention provides for a method of fastening a fastenable device to a toothbrush neck comprising the steps: (a) providing a fastenable device of the present invention; (b) providing a toothbrush comprises a handle portion and an opposing bristle head, with the neck portion therein between; (c) squeezing either: (i) the base portion or the body portion and the toothbrush neck portion together until the first snappable recess snaps around at least a portion of the toothbrush neck; or (ii) the head portion or the body portion and the toothbrush neck portion together until the second snappable recess snaps around at least a portion of the toothbrush neck thereby fastening the fastenable device to the toothbrush neck.

These and other features, aspects, and advantages of the present invention will become evident to those skilled in the art from the detailed description which follows.

BRIEF DESCRIPTION OF THE DRAWINGS

While the specification concludes with claims particularly defining and distinctly claiming the invention, it is believed that the invention will be better understood from the following description of the accompanying figures.

DETAILED DESCRIPTION OF THE INVENTION

Figure 1A:
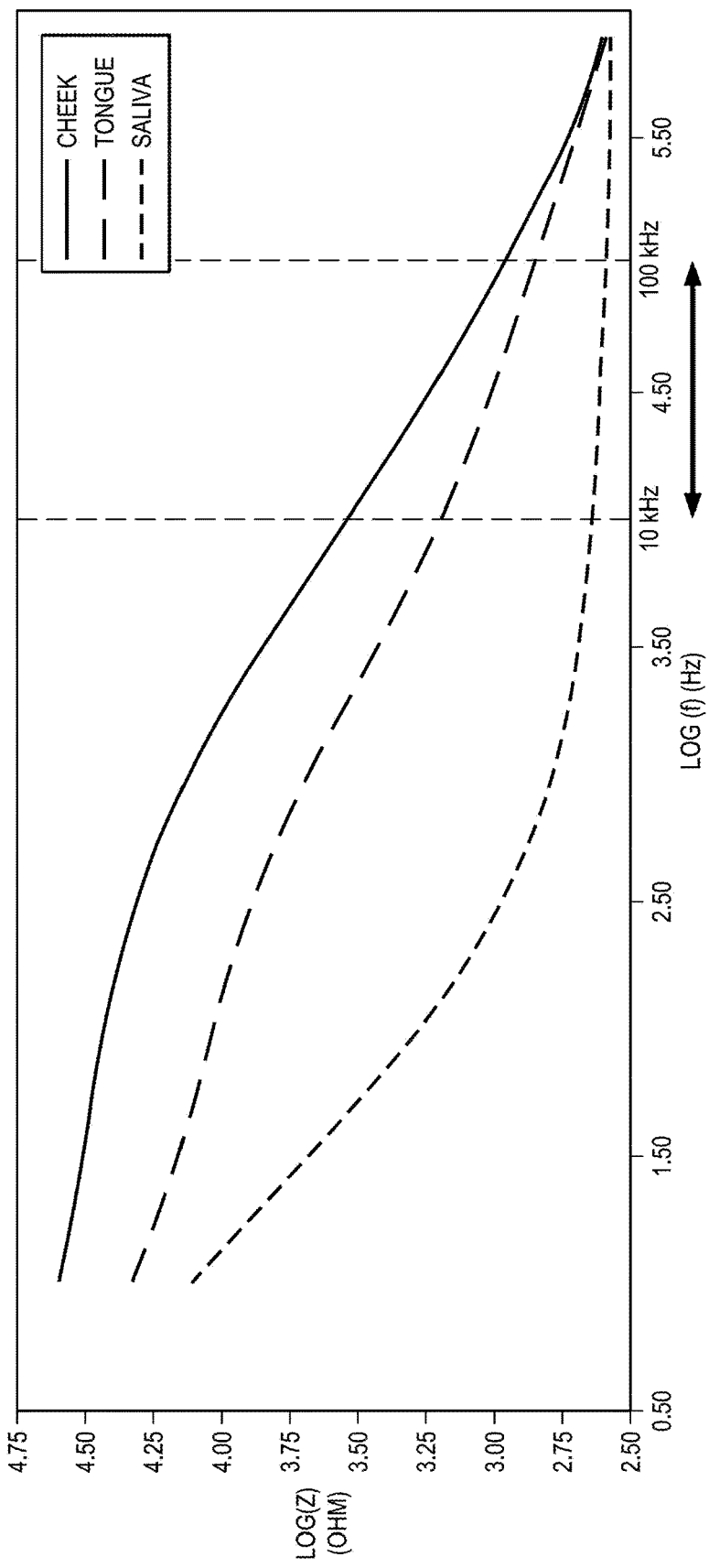
FIG. 1(a) shows an impedance magnitude variation of cheek area, tongue area, and saliva area over frequency.

As used herein, the articles including "a", "an", and "the" are understood to mean one or more of what is claimed or described.

As used herein, the terms "comprise", "comprises", "comprising", "include", "includes", "including", "contain", "contains", and "containing" are meant to be non-limiting, i.e., other steps and other sections which do not affect the end of result can be added. The above terms encompass the terms "consisting of" and "consisting essentially of".

According to the present invention, a fastenable device configured to be fastenable to an oral care implement, which enables oral area contact detection and even oral cavity position detection, is provided. The present invention is based, in part, on the surprising discovery that certain oral areas of the oral cavity have unique impedance signatures when impedance is assessed and compared at different voltage frequencies. Furthermore, these impedance signatures (at different voltage frequencies) are even more pronounced between oral areas at certain frequency ranges. Without wishing to be bound by theory, it is the unique conductivity/dielectricity of each oral area that provides for the unique impendence signature at different voltage frequencies (at frequency ranges). This important discovery leads to more accuracy and/or precision in oral area contact detection and oral cavity position detection of an oral care implement to which the fastenable device is fastened.

The term "oral area", as used herein, refers to a distinct part or section inside an oral cavity, including but not limited to, cheek area, tongue area, saliva area, tooth area, gum area, hard palate area, soft palate area, and lip area. Specifically, the fastenable device may comprise an electrode pair, a frequency generator, an impedance measurement unit and a contact determination unit. The electrode pair is preferably disposed on the housing of the fastenable device that contacts various oral areas during the device's use in the oral cavity (while fastened to an oral care implement such as a toothbrush). An impedance is formed between the electrode pair when electrified. Electricity is provided by way of a battery (contained within the device). The battery is in electrical communication with one or more of the electrical components of the device. The frequency generator is electrically connected to the electrode pair, for applying a voltage with at least two different frequencies between the electrode pair. The change in frequencies happens preferably within about 1 s, 500 ms, 50 ms, 10 ms, 5 ms, or even 1 ms. The impedance measurement unit is electrically coupled to the electrode pair, for measuring impedance values between the electrode pair at the different frequencies. The term "impedance value" is used herein the broadest sense to include any value that can be derived from assessing conductivity/dielectricity between electrodes including but not limited to impedance magnitude, impedance phase, relative permittivity, and combinations thereof.

A "defined oral area" is a predetermined oral area of which the impedance value has been assessed and can be used as a reference. In the case that the electrode pair is contacting a defined oral area such as a saliva area, a cheek area or a tongue area, the impedance values may be quite different at different frequencies due to the oral area's specific conductivity/dielectricity. Therefore, the contact determination unit is used to determine contact information of the electrode pair based on this specific conductivity/dielectricity. The contact determination unit comprises a memory for storing a function. The function correlates impedance values of the defined oral area at the different frequencies, which reflects the specific conductivity/dielectricity of the defined oral area. In turn, the contact determination unit is in communication with the impedance measurement unit. As used herein, the term "in communication with" means there is data transmission between two elements connected by this term. The communication method may be of any form, including wireless communication or hard-wired communication. Some examples of the communication methods are discussed in, for example, US20130311278A at paragraphs 39 to 41.

The contact determination unit comprises a processor for processing the measured impedance values to the stored function(s) so as to determine contact information of the electrode pair with the defined oral area(s). Specifically, if a particular measured impedance value meets the specific conductivity/dielectricity represented by a stored function, it will be determined that the electrode pair is contacting the defined oral area (to which the stored function corresponds). If the measured impedance value does not meet the specific conductivity/dielectricity represented by the stored function, it will be determined that the electrode pair is not contacting the defined oral area (to which the stored function corresponds). The fastenable device may further comprise a position determination unit, which is in communication with the contact determination unit. The position determination unit is configured for determining an oral cavity position of the device (and therefore the oral care implement to which the device is fastened) based on at least the determined contact information.

Without wishing to be bound by theory, the present invention improves the accuracy and/or precision of position detection by, in part, the use of a frequency generator to generate at least two different voltage frequencies, and measuring at different frequencies. Indeed, it is surprisingly found that different oral areas have different impedance signatures (e.g., between two frequencies). Furthermore, this difference is even more pronounced within certain frequency ranges. Impedance value measurements at different frequencies allow differentiation among different oral tissues within the oral cavity (e.g., tongue and cheek) and saliva. This is in contrast to single frequency devices or those devices that do not measure at different frequencies which merely can determine if "contact" is made.

Among various oral areas, the saliva area basically consists of water and/or a toothpaste slurry and therefore has a lot of ions which may contribute to its conductivity. The oral areas comprising oral tissues, such as the cheek area and the tongue area also have conductivity because of the huge amount of water they contain. However, oral tissues further comprise cells in addition to the water. This will contribute to the dielectricity of the oral tissues and cause a visible difference in the impedance versus frequency diagram of saliva and oral tissues. The main characteristics in the variation of oral tissue impedance over the frequency can be grouped in three categories: α dispersion, β dispersion, and γ dispersion. The α dispersion contributes to the impedance change of any conductor at low frequencies in the hertz range. The β dispersion is found in living tissue in the kilohertz to megahertz range, and is caused by the cellular membranes. The γ dispersion is a high frequency phenomenon in the gigahertz range due to the polarization of water molecules. Therefore, these different oral areas may show different conductivity/dielectricity due to their different compositions. For example, the amount of water and/or cells contained in the oral area, the shape of the cells, the arrangement of the cells may all cause the conductivity/dielectricity of a certain oral area to differ from other oral areas.

FIG. 1(a) is a graph showing a typical impedance magnitude variation at different frequencies for the cheek area, the tongue area, and the saliva area. The graph demonstrates that these oral areas can be differentiated between each other based on their impedance values (at different voltage frequencies). The x axis of the FIG. 1(a) graph represents frequency in hertz (Hz) on a log scale from 0.50 to 6.00. The y axis of the FIG. 1(a) graph represents impedance magnitude in ohm (Ω) on a log scale from 2.50 to 4.75. It can be seen that the cheek area, the tongue area and the saliva area have quite different impedance magnitudes at various frequencies. For example, the impedance magnitude of the saliva area drops sharply between the frequencies from 10 Hz to 1 kHz, and then stabilizes over a broad range up to almost 1 MHz. For the cheek area and the tongue area, the sharp drop of the impedance magnitude appears in the range from 1 kHz to 1 MHz, with different drop rates. Therefore, in an embodiment, the function correlating impedance values of the defined oral area at the different frequencies may be a linear function reflecting the drop rate at a certain frequency range. For example, it can be seen that the drop rate of the impedance magnitude at a frequency range from 10 kHz to 100 kHz is quite different among the cheek area, the tongue area, and the saliva area. In an alternative embodiment, the function correlating impedance values of the defined oral area at the different frequencies may be selected from the group consisting of a quadratic function, a cubic function, a quartic function, a quintic function, a sextic function, and a rational function, provided that the selected function can be used to differentiate the defined oral area from other oral areas at a certain frequency range.

Figure 1B:
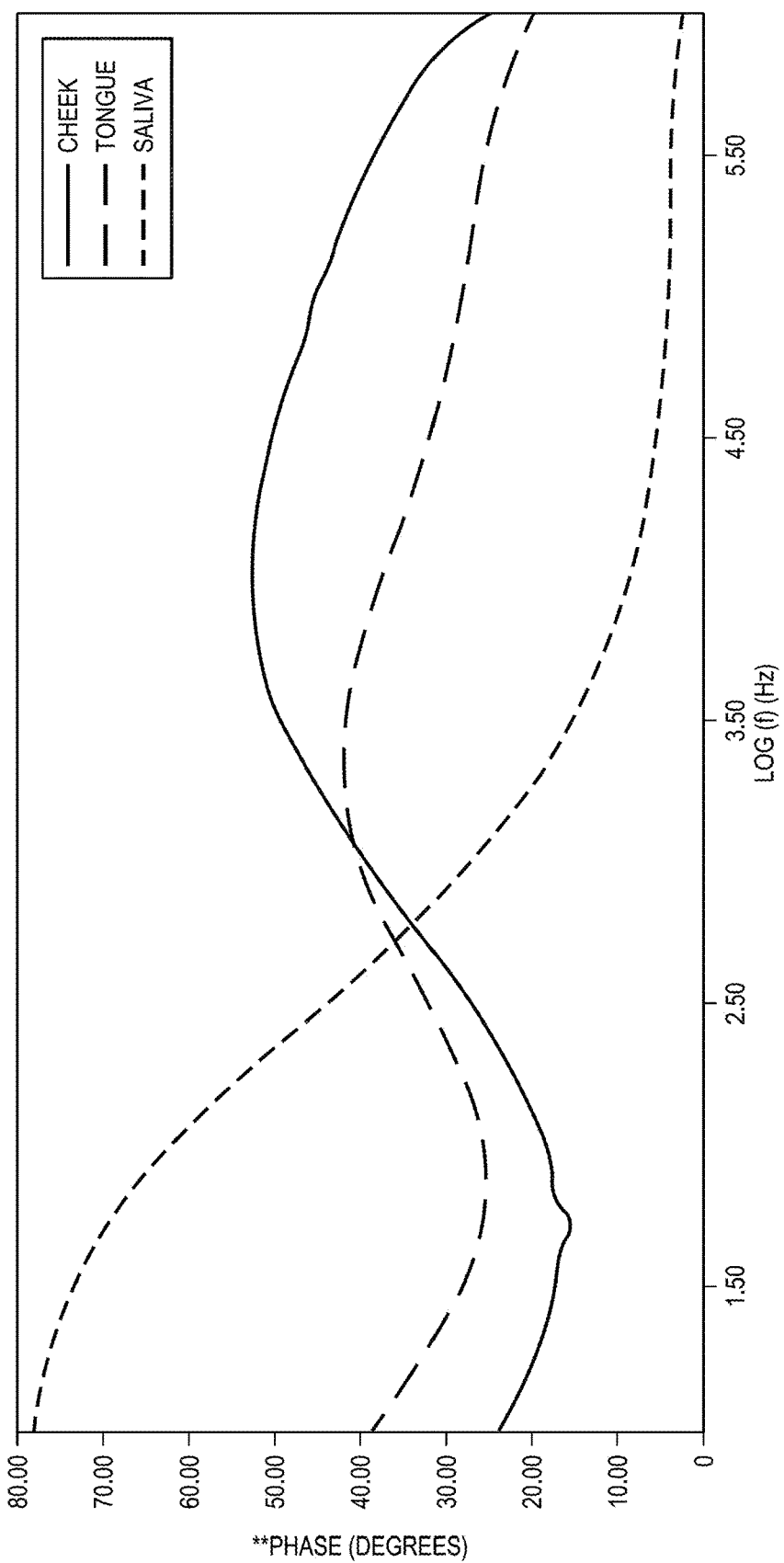
FIG. 1(b) shows an impedance phase angle variation of cheek area, tongue area, and saliva area over frequency.
Figure 2:
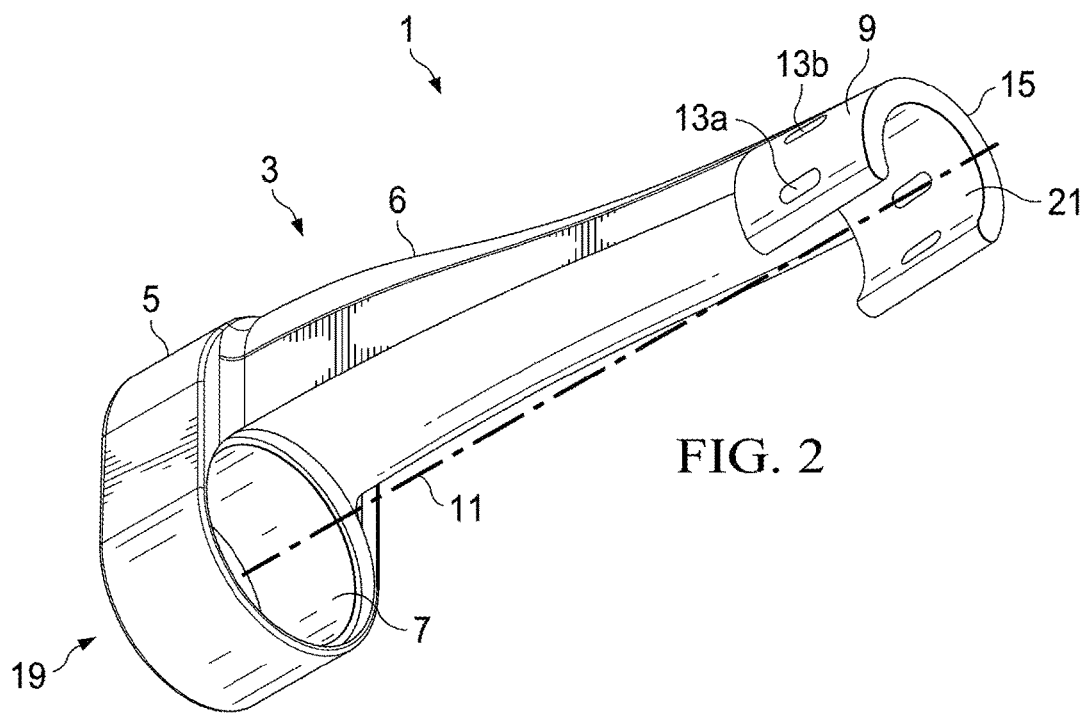
FIG. 2 is a first perspective view of a fastenable device for oral area position detection of the present invention.
Figure 3:
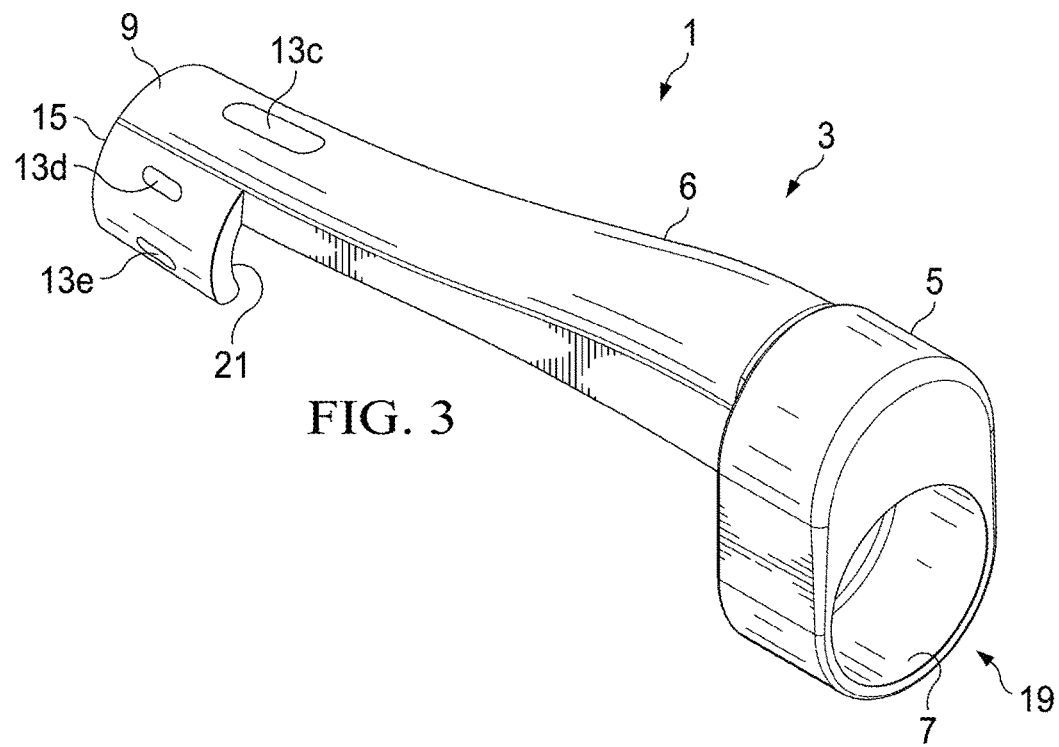
FIG. 3 is a second perspective view of the fastenable device of FIG. 2.
Figure 4:
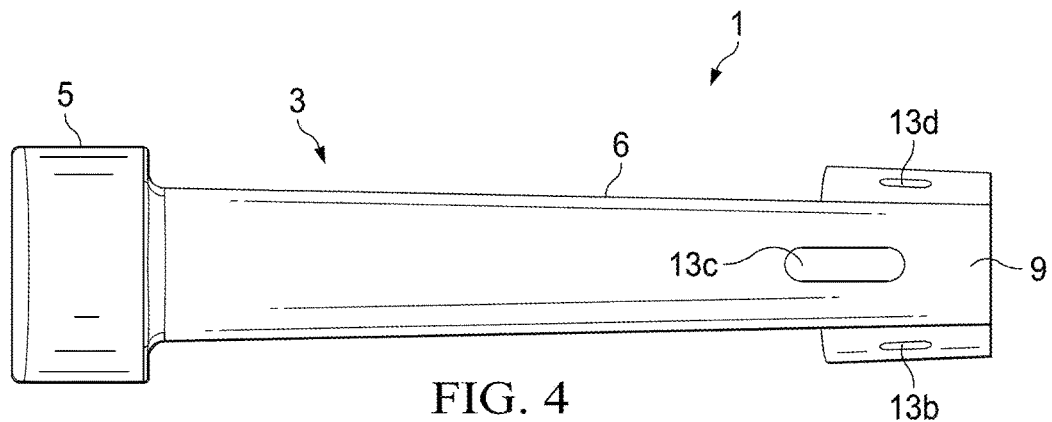
FIG. 4 is top view of the device of FIGS. 2 and 3.
Figure 5:
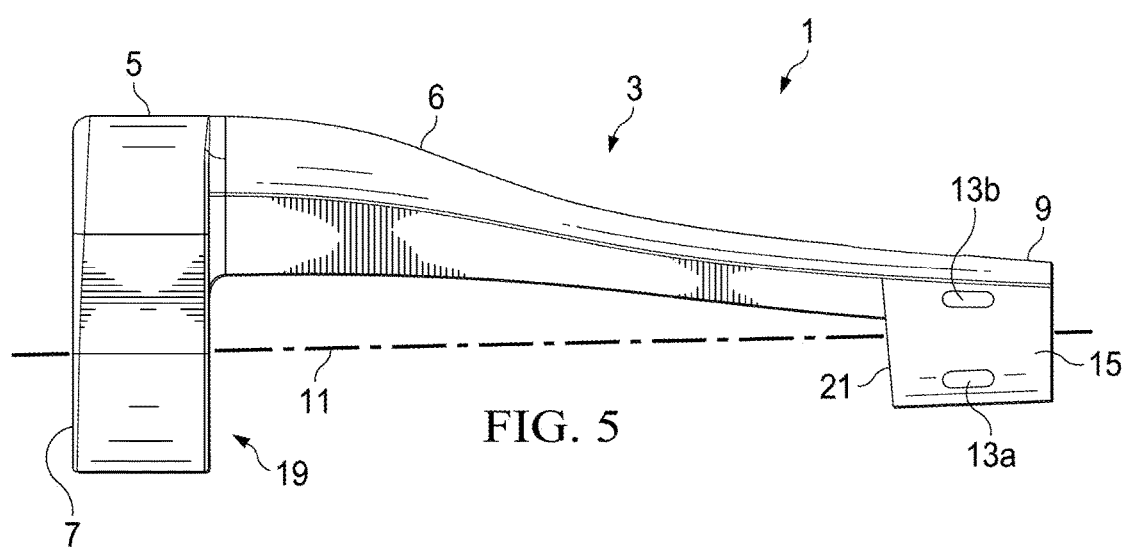
FIG. 5 is a side view of the device of FIGS. 2 and 3.

FIG. 1(b) is a graph showing a typical impedance phase angle variation at different frequencies for the cheek area, the tongue area, and the saliva area. The x axis of the FIG. 1(b) graph represents frequency in hertz (Hz) on a log scale from 1.00 to 6.00. The y axis of the FIG. 1(b) graph represents impedance phase angle in degree)(° from 0° to 80°. It can be seen that the cheek area, the tongue area and the saliva area have quite different impedance phase angle at various frequencies. For example, the impedance phase angle of the saliva area drops sharply from 100 Hz to 10 kHz, and then stabilizes over a broad range up to almost 1 MHz. The impedance phase angle of the cheek area decreases sharply at low frequencies from 10 Hz to 50 Hz, and then increases sharply from 50 Hz to almost 10 kHz, and then decreases again at high frequencies up to 1 MHz. The impedance phase of the tongue area decreases sharply at low frequencies from 10 Hz to 100 Hz, and then increases sharply from 100 Hz to 1 kHz, and then decreases again at high frequencies up to 1 MHz. In one embodiment, a certain frequency range, for example, 100 Hz to 1 kHz, can be selected to differentiate the cheek area, the tongue area, and the saliva area by the drop rate of the impedance phase angle.

The fastenable device for oral area position detection is fastenable to an oral care implement. In turn, the oral care implement of the present invention may take the form of a toothbrush (manual or electric), a flosser, an oral irrigator, a tongue scraper, an interdental cleaner, an oral appliance and any other oral or dental devices which, at least a part of which, is utilized in the oral cavity. These descriptions are given solely for the purpose of illustration and are not meant to be construed as limitations of the present invention, as many variations of the embodiments described hereinafter are possible without departing from the spirit and scope of the present invention.

FIGS. 2 to 6 are directed to a fastenable device (1) of the present invention configured to be fastenable to an oral care implement (e.g., toothbrush, not shown) and for oral area position detection. Different views of the same device (1) are provided in FIGS. 2-6 and are collectively reference to herein. The fastenable device (1) comprises housing (3) that houses various electrical components. The housing (3) is defined by a base portion (5) and an opposing head portion (9) and a body portion (6) in between the base portion (5) and the head portion (9). The housing may be made from plastic such as POM, or PMT, or PP, or combinations thereof. The base portion (5) comprises a first fastener (7). The first fastener (7) is in the form of a full ring integral to the housing (3) defining a through-hole (19) having an inner diameter of 12 mm. The through-hole (19) is configured to be slideable along a toothbrush neck portion (not shown in FIGS. 2-6) (wherein the neck portion slides through the through-hole (19)). The head portion (9) comprises a second fastener (15). The second fastener (15) is in the form of an open ring integral to the housing (3) defining a snappable recess (21) having an inner diameter of 7 mm. The snappable recess (21) is configured to be releasably fastenable to the toothbrush neck portion (35). A longitudinal axis (11) traverses the center of the through-hole (19) and midpoint of the inner diameter of the snappable recess (21). The length of the fastener device (1) along the longitudinal axis (11) is 58 mm, alternatively from 15 mm to 240 mm. The fastenable device (1) has bilateral symmetry along a plane of bilateral symmetry (not shown) that intersects the longitudinal axis (11).

The diameters of the through-hole (19) and the snappable recess (21) are measured orthogonal to the longitudinal axis (11). The cross sectional area of the through-hole (19), orthogonal to the longitudinal axis (11), is 113 mm$^2$, alternatively from 55 mm$^2$ to 5541 mm$^2$ The longest dimension measured long the longitudinal axis (11) of the fastenable device (1) is from 48 mm to 68 mm, preferably 52 mm to 64 mm, alternatively combinations thereof. The snappable recess (21) has a circular arc about 1$\pi$ radian around the longitudinal axis (11). The open portion of the snappable recess (21) that is orthogonal to the longitudinal axis (11) is configured to releasably fasten (i.e., "snap") at least partially circumferentially around e.g., a toothbrush neck (not shown in FIGS. 2-6). When the user is ready to remove the device (1) from the toothbrush, the user can simply pull the device away from the toothbrush neck as to "un-snap" the snappable recess (21).

In one aspect of the invention provides a fastenable device (1) comprising a housing (3) defined by a base portion (5) and an opposing head portion (9) and a body portion (6) in between the base portion (5) and the head portion (9), wherein the base portion (5) comprises a first fastener (7) in the form of a full ring integral to the housing (3) defining an through-hole (19), and wherein the head portion (9) further comprises a second fastener (15) in the form of an open ring integral to the housing (3) defining a snappable recess (21).

In an alternative aspect of the invention, the fastenable device has at least two snappable recesses. In other words, the invention provides a fastenable device (1) comprising a housing (3) defined by a base portion (5) and an opposing head portion (9) and a body portion (6) in between the base portion (5) and the head portion (9), wherein the base portion (5) comprises a first fastener (7) in the form of of a first open ring integral to the housing (not shown) defining a first snappable recess (not shown), and wherein the head portion (5) further comprises a second fastener (15) in the form of a second open ring integral to the housing (3) defining a second snappable recess (21).

Electrodes

During use, at least a part of the head portion (9) of the device (1) is put into the oral cavity of a user such that one or more electrodes (13) make contact with the user's teeth or gum. The electrodes (13) are generally spaced equally and rotationally arranged (relative to the longitudinal axis (11)) along the head portion (9). The third electrode (13c) is bifuricated by the plane of bilateral symmetry, and is facing the rear of the toothbrush (31), i.e., opposing the bristles (41) side. The first and second electrodes (13a, 13b) are one side of the head portion (9), and where the fourth and fifth electrodes (13d, 13e) are on the other opposing side of the head portion (9). These electrodes (13) may form electrode pairs with each other. For example, a first electrode pair may be formed between the second electrode (13b) and the fourth electrode (13d). A second electrode pair may be formed between the fourth electrode (13d) and the fifth electrode (13e). A third electrode pair may be formed between the first electrode (13a) and the second electrode (13b). A fourth electrode pair may be formed between the third electrode (13c) and the fourth electrode (13d). A fifth electrode pair may be formed between the second electrode (13b) and the third electrode (13c). Obviously this can be extended in those embodiments having more than five electrodes (13).

This arrangement of circumferentially disposed electrodes (13) is especially advantageous when not all contact with a defined oral area can be detected by any specific first electrode pair. For example, in some cases, only one electrode (e.g., 13b) is contacting a defined oral area and therefore the contact will be not detected by the first electrode pair (i.e., 13b and 13d). The fifth electrode pair (i.e., 13b and 13c) will make sure contact of the rear side of the toothbrush (31) with a defined oral area will be able to be detected. Each of the electrodes may employ a conductive resin or metal material, and may be formed integrally with the fastenable device's housing (3).

Of course additional electrodes may be disposed at the head portion (9) or elsewhere on the device to potentially enable even more precise contact information with a defined oral area (depending upon factors that may include cost constraints, extent of the surface area, and precision needed). Each of the electrodes may employ a conductive resin or metal material, and may be formed integrally with the head portion (9), or may be assembled/connected to the head portion (9).

Figure 6:
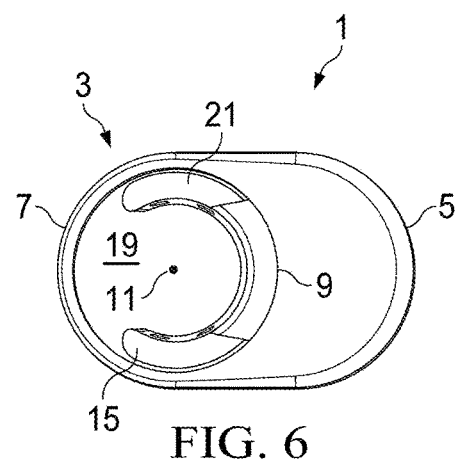
FIG. 6 is a front view of the device of FIGS. 2 and 3.
Figures 7, 8:
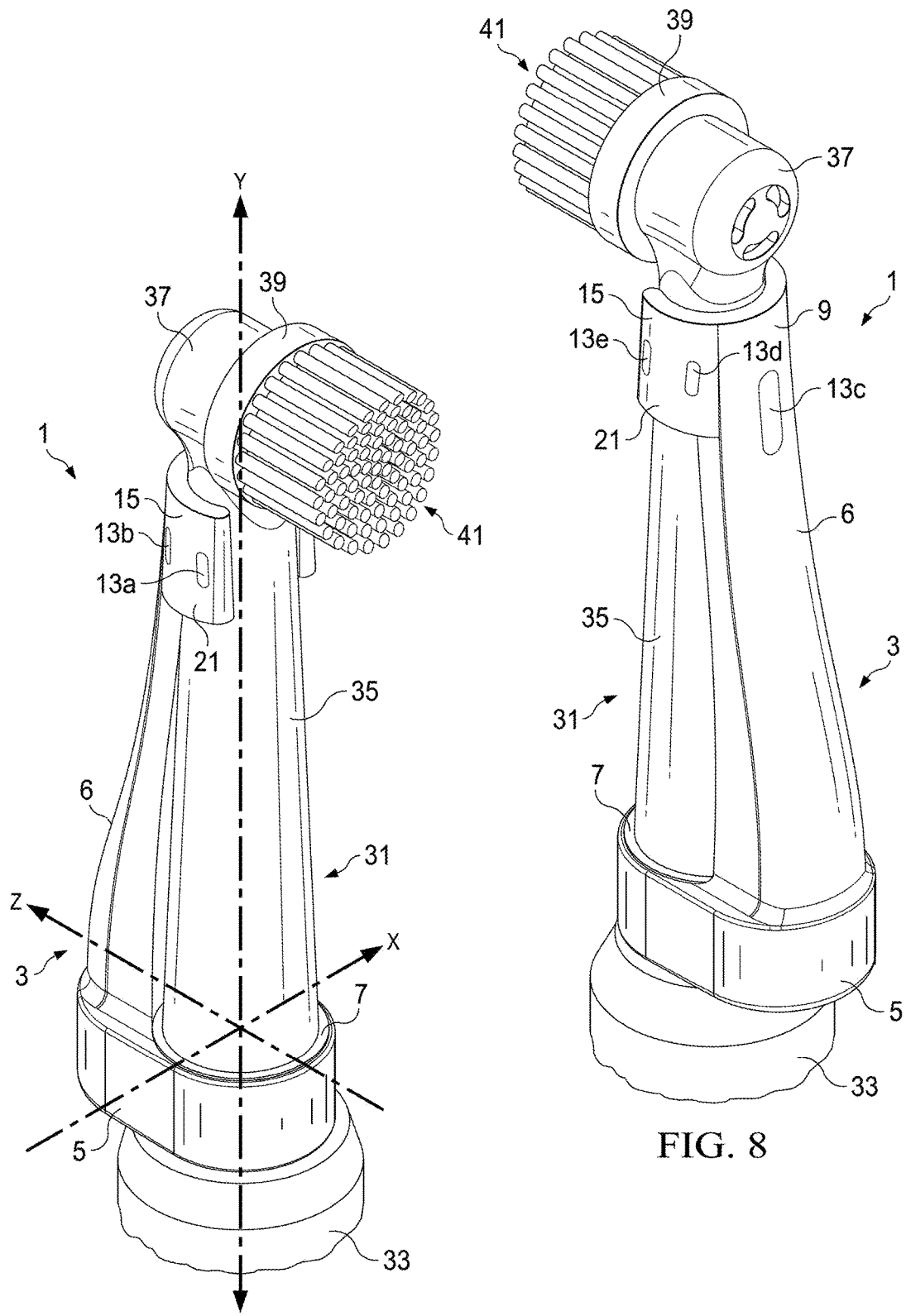
FIG. 7 is a first perspective view of the fastenable device of FIGS. 2 and 3 fastened to a toothbrush neck.
FIG. 8 is a second perspective view of the fastenable device FIGS. 2 and 3 fastened to the toothbrush neck.

FIGS. 7 and 8 illustrate the fastenable device (1) fastened to a toothbrush (31). The toothbrush (31) is an electrical one having a hand portion (not shown) and an opposing bristle head (39), with a neck portion (35) therein between. Of course the fastenable device (1) can be releasably fastened to manual toothbrush (i.e., non-electrical ones). The neck portion (35) specially has a bulbous neck terminus (37) immediately adjacent the bristle head (39). In turn, the bristle head (39) has a plurality of bristles (41) disposed thereon that are configured to clean teeth during operation (e.g., by a rotating, oscillating, vibration, motion and the like). The handle portion is where the user will grasp the toothbrush (31) during operation (i.e., configured to be graspable by a user). The handle portion may also house the electrical supply and motor (not shown) of the tooth brush (31). The motor provides the movement to rotate and/or oscillate and/or otherwise provide movement to the bristle head (39). In some executions, electrical tooth brushes (31) will have a replaceable neck portion (35) and bristle head (39). In one embodiment, the fastenable device (1) of the present invention is fastened to only the neck portion (35) of the toothbrush (31) (as illustrated in FIGS. 6 and 7). The toothbrush neck portion (35) is preferably much small in diameter than the toothbrush handle portion (33).

Referring to FIGS. 7 and 8, the electrodes (13) are disposed on the head portion (9) of fastenable device (1). When the fastenable device (1) is attached to the toothbrush (31), the electrodes (13) are adjacent the bristles (31). This provides more accurate position detection data to where the bristles are vis-a-vis the teeth being cleaned given the close proximity between the electrodes (13) and the bristles (41). The "bristles (41) side" or "side the bristles (41) face" is referring to the side which the bristles (41) are configured to make contact with the tooth. This is likely best observed in FIG. 7. By analogy, the same holds true to any other oral care implement and the implement's functioning end (e.g., spout of a water pick).

Although five electrodes (13a, 13b, 13c, 13d, 13e) are shown circumferential (around the longitudinal axis (11)) and equidistantly disposed around the head portion (9), different embodiments are of course possible. For example, in one embodiment, there is a single electrode pair (i.e., two electrodes). In another embodiment, there are 3, 4, 5, 6, 7, 8, 9, 10 or more electrodes (13) disposed on the head portion (9) but also possibly on the body portion (6) and/or base portion (5) of the device (1). In yet another embodiment, there are no electrodes on or adjacent the toothbrush handle portion (33) (when the device (1) is fastened to the toothbrush (31)). In a preferred embodiment, the electrodes (13) (disposed on the housing (3)) are in close proximity or adjacent the toothbrush bristles (41) when the fastenable device (1) is fastened to the toothbrush neck portion (35) to provide the most accurate oral area position detection with respect to where the bristles (41) i.e., bristles (41) side, make contact to the defined oral area.

Methods of Fastening

One aspect of the invention provides for a method of installing the fastenable device (1) of the present invention to an oral care implement (e.g., toothbrush). A first step is directed to the user threading the bristle head (39) of the toothbrush (1) through the through-hole (19) of the first fastener (7) of the fastenable device (1). The through-hole (19) is slideably engageable with the toothbrush neck portion (35). The fastenable device (1) is slid along the toothbrush neck (35) until it reaches the toothbrush handle portion (33). Generally, the toothbrush neck (35) has a much smaller diameter than the toothbrush handle portion so that the fastenable device (1) cannot be slid further once the diameter increases between the transition from toothbrush neck portion (35) and toothbrush handle portion (33).

The second step in the method provides for the user to digitally press against the head portion (9) or even body portion (6) of the fastenable device (1) as to have the snappable recess (21) of the fastenable device (1) releasably fasten the toothbrush neck portion (35). Either side of the snappable recess (21) is elastically expandable so to engage the toothbrush neck portion (35) and apply force against neck portion (35) as to have friction to keep the fastenable device (1) releasably fastened to the toothbrush (31) during operation.

Referring to FIGS. 7 and 8, the surface area of the snappable recess (21) engages the toothbrush neck (35) surface. The surface of the through-hole (19) engages the toothbrush neck (35) surface. The first fastener (7) frictionally engages the surface of the toothbrush neck portion (35) nearest the toothbrush bristle head (39). The second fastener (15) frictionally engages the surface of the toothbrush neck portion (35) nearest the toothbrush handle portion (33) (via the surface defining the through-hole (19) and the surface of the neck portion (35)).

One aspect of the invention provides for a method of fastening a fastenable device (1) to a toothbrush neck (35) comprising the steps: (a) providing the fastenable device (1) comprising: a housing (3) defined by a base portion (5) and an opposing head portion (9) and a body portion (6) in between the base portion (5) and the head portion (9), wherein the base portion (5) comprises a first fastener (7) in the form of a full ring integral to the housing (3) defining an through-hole (19), and wherein the head portion (9) further comprises a second fastener (15) in the form of an open ring integral to the housing (3) defining a snappable recess (21); (b) providing a toothbrush (31) comprises a handle portion (33) and an opposing bristle head (39), with the neck portion (35) therein between; (c) sliding the toothbrush bristle head (39) through the through-hole (19) of the first fastener (7) and continuing until the handle portion (33) abuts the first fastener (7); and (d) squeezing the head portion (9) or the body portion (6) and the toothbrush neck portion (35) together until the snappable recess (21) snaps around at least a portion of the toothbrush neck (35) thereby fastening the fastenable device (1) to the toothbrush neck (35).

Another aspect of the invention provides for a method of fastening a fastenable device (1) to a toothbrush neck (35) comprising the steps: (a) providing a fastenable device (1) comprising a housing (3) defined by a base portion (5) and an opposing head portion (9) and a body portion (6) in between the base portion (5) and the head portion (9), wherein the base portion (5) comprises a first fastener (7) in the form of a of a first open ring integral to the housing (not shown) defining a first snappable recess (not shown), and wherein the head portion (9) further comprises a second fastener (15) in the form of a in the form of a second open ring integral to the housing (3) defining a second snappable recess (21); (b) providing a toothbrush (31) comprises a handle portion (33) and an opposing bristle head (39), with the neck portion (35) therein between; (c) squeezing either: (i) the base portion (5) or the body portion (6) and the toothbrush neck portion (35) together until the first snappable recess snaps (not shown) around at least a portion of the toothbrush neck (35); or (ii) squeezing the head portion (9) or the body portion (6) and the toothbrush neck portion (35) together until the second snappable recess (21) snaps around at least a portion of the toothbrush neck (35) thereby fastening the fastenable device (1) to the toothbrush neck (35). Of course the user may squeeze both the base portion (5) and the head portion (9). To this end the user may squeeze both portions (5, 9) concurrently (e.g., using both hands) or may do so sequentially. The use may use squeeze using a single hand or using both hands.

One advantage of having the fastenable device releasably fastenable to the oral care implement is that the user need not be subjected to the replacement costs associated with position detection electronics each time e.g., bristles need to be replaced. In other words, the fastenable device may be unfastened and re-fastened each time the bristles are replaced or even the toothbrush itself is replaced. The invention provides valuable oral area position detection to the user for every brushing episode but yet saves the user money by not subjecting the user to replacement costs every time bristles and/or toothbrush are replaced. Indeed bristles more often than not wear out before electronics do.

Of course alternatively, the fastenable device may have a single fastener, preferably a first and second fastener, more preferably wherein the first and second fasteners are on opposing ends of the device (e.g., head portion and base portion). An alternative embodiment may have three or four or more fasteners. In one embodiment, the fastenable device is only releasably fastenable to the toothbrush neck. In one embodiment, the first fastener and the second fastener may both be in the form of a full rings integral to the housing defining snappable recesses, respectively; such that that the first and second fasteners may both be "snapped" circumferentially around at least a portion of the toothbrush neck. In yet another embodiment, the device is releasable fastened to both the handle portion and the neck portion of the toothbrush. Alternatively, the toothbrush and/or device may be fitted male/female connectors as fasteners. Examples of such male/female connectors are well known. See e.g., US 2007/0264901 A1. Alternatively, the fastener(s) can take the form of hook and loop (e.g., Velcro®) (e.g., the hook may be on the device while the loop may be on the toothbrush or vice versa). The fastenable device may be designed to retrofit pre-existing oral care implements. Alternatively, the fastenable device and the oral care implement may be designed at the same time to complement each other. To this end, a cross section of the through-hole of the base portion of the fastenable device need not be circular, but rather compliment or mirror a unique shape of the toothbrush neck (the same, of course, can be true for the second and/or third fasteners (if present)).

A non-limiting example of an electric toothbrush having a cleaning head (i.e., a bristle head with bristles), a handpiece (i.e., handle portion), and neck portion arranged between the cleaning head and the handpiece is described in WO 2010/106524. BRAUN® is a brand of electric toothbrushes. Although not described in FIG. 2-8, the device housing houses many electrical components.

Figure 9:
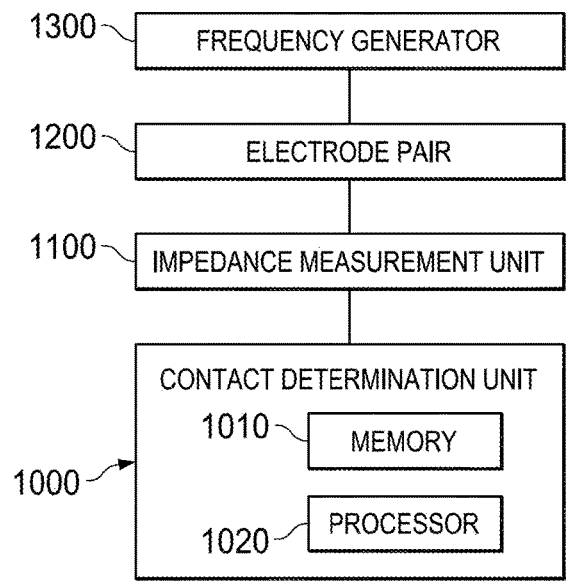
FIG. 9 is a block diagram illustrating an electrical circuit for determining contact information of an electrode pair according to an embodiment of the present invention.

Each of the electrode pairs comprised of the electrodes is in electrical communication within an electrical circuit, and impedance may be formed between each of the electrode pair when electrified. FIG. 9 shows a block diagram illustrating the electrical circuit for determining contact information of the electrode pair with a defined oral area according to an embodiment of the present invention. In FIG. 9, an electrode pair (1200) is used to refer to any one of the first through fifth electrode pairs of the electrodes (13) as shown in FIGS. 7 and 8. Referring to FIG. 9, a frequency generator (1300) is electrically connected to the electrode pair (1200), for applying a voltage with at least two different frequencies between the electrode pair (1200). The electrical connection between the frequency generator (1300) and the electrode pair (1200) may be achieved by a wire connection, for example, via a flexible copper wire or cable. The frequency generator (1300) is preferably operable to generate frequencies ranging from 1 kHz, 10 kHz, or 50 kHz to 100 kHz, 500 kHz, or 1 MHz, although other frequency ranges are also possible. In an embodiment, the frequency generator (1300) may alternately generate and alternate between two frequencies. Alternatively, the frequency generator (1300) may generate and alternate among 3, 4, 5, 6, 7, 8, 9, 10 or more frequencies. Yet alternatively still, the frequency generator (1300) may generate a non-stationary frequency spectrum, for example, in a waveform selected from sine waveform, square waveform, triangle waveform, sawtooth waveform, and combinations thereof. The selection of the frequency value and waveform may depend on the specific conductivity/dielectricity of the defined oral area. For example, a frequency range may be selected if the impedance of the defined oral area changes with a tendency to be significantly different from other oral areas when the frequency changes in this frequency range, so as to easily differentiate the defined oral area from the other oral areas. The frequency generator (1300) may be implemented by those manufactured by Harris Corporation (Melbourne, Fla.) or Hewlett Packard Corporation (Palo Alto, Calif.).

An impedance measurement unit (1100) is electrically coupled to the electrode pair (1200), for measuring impedance values between the electrode pair at different frequencies. In an embodiment, the impedance measurement unit (1100) may be physically connected to the electrode pair (1200) by a wire connection, for example, via a flexible copper wire or cable. In another embodiment, the impedance measurement unit (1100) may be wirelessly coupled to the electrode pair (1200), for example, using laser and piezoelectric transducers (see, e.g., Hyun-Jun Park, Hoon Sohn, Chung-Bang Yun, Joseph Chung and Il-Bum Kwon. A wireless guided wave excitation technique based on laser and optoelectronics. Smart Structures and Systems, Vol 6, No. 5-6, 2010, 749-765). The impedance measurement unit (1100) may follow a measurement method selected from the group consisting of bridge method (such as Wheatstone Bridge method), resonant method, I-V (current-voltage) method, RF (radio frequency) I-V method, network analysis method, auto balancing bridge method, and combinations thereof. The choice of the impedance measurement method may depend on some factors such as the frequency range, measurement range, measurement accuracy and ease of operation. For example, the auto balancing bridge method may ensure a high accuracy measurement for a broad frequency range from 1 MHz to 110 MHz, the RF I-V method may have the best measurement capability for frequency range from 100 MHz to 3 GHz, and the network analysis may be the recommended technique when the frequency ranges from 3 GHz and up. The impedance measurement unit (1100) may be implemented by those manufactured by Agilent Technologies (Santa Clara, Calif.).

A contact determination unit (1000) is in communication with the impedance measurement unit (1100), for determining contact information. When the electrode pair (1200) is electrified and contacting a defined oral area, a closed circuit is formed with an electrical current going through the defined oral area. The impedance of the defined oral area is measured as a reaction to the electrical current and represents the conductivity/dielectricity of the defined oral area. Different oral areas may have different conductivity/dielectricity measurements due to different compositions and structures. For example, the more water a particular oral area contains, the more conductive it is, and therefore the more constant its impedance is over a broad frequency range (as compared to those areas having less water). The present invention is based on the different conductivity/dielectricity of various oral areas at different electrical frequencies. Therefore, the contact determination unit (1000) may comprise a memory (1010) for storing a function, wherein the function correlates impedance values of a defined oral area at different frequencies. The function may relate to one or more oral areas selected from the group consisting of cheek area, tongue area, and saliva area as discussed hereinabove with respect to FIGS. 1(*a*) and 1(*b*). The contact determination unit (1000) may further comprise a processor (1020) for processing the measured impedance values to the stored function so as to determine contact information of the electrode pair (1200) with the defined oral area. The memory (1010) and the processor (1020) may each independently be embodied in any form and may be associated with each other in any form. Some examples of the memory (1010) and the processor (1020), as well as their association, may be found in, for example, US2013/0176750A1 at paragraphs 426 to 431.

In one embodiment, the memory (1010) further stores a controlled program to determine whether the measured impedance value is above a pre-established threshold value indicating that the device (1) is near or within the oral cavity of a user, and thereafter actuating oral care position detection of the device (1), preferably the device (1) is characterized by a lack of a mechanical on/off switch. See e.g., US 2012/0246846A1.

The frequency generator (1300), the impedance measurement unit (1100) and the contact determination unit (1000) may be integrated into a printed circuit board (PCB, not shown). The PCB may be accommodated in the device's housing (3) as shown in FIGS. 2-6. The electrodes (13) may be connected to the PCB by way of conductors and/or lines (not shown). The housing (3) has an outer surface and opposing inner surface (not shown) wherein the inner surface of the housing defines an interior volume to house these conductors and/or lines. These conductors and/or lines may be attached to the inner surface of the housing (3). The number of the conductors disposed on the inner surface of the housing (3) is typically equivalent to the number of the electrodes (13). An electrode (13), and its respective line and/or conductor, may be formed integrally or may be assembled/connected together.

Figure 10A:
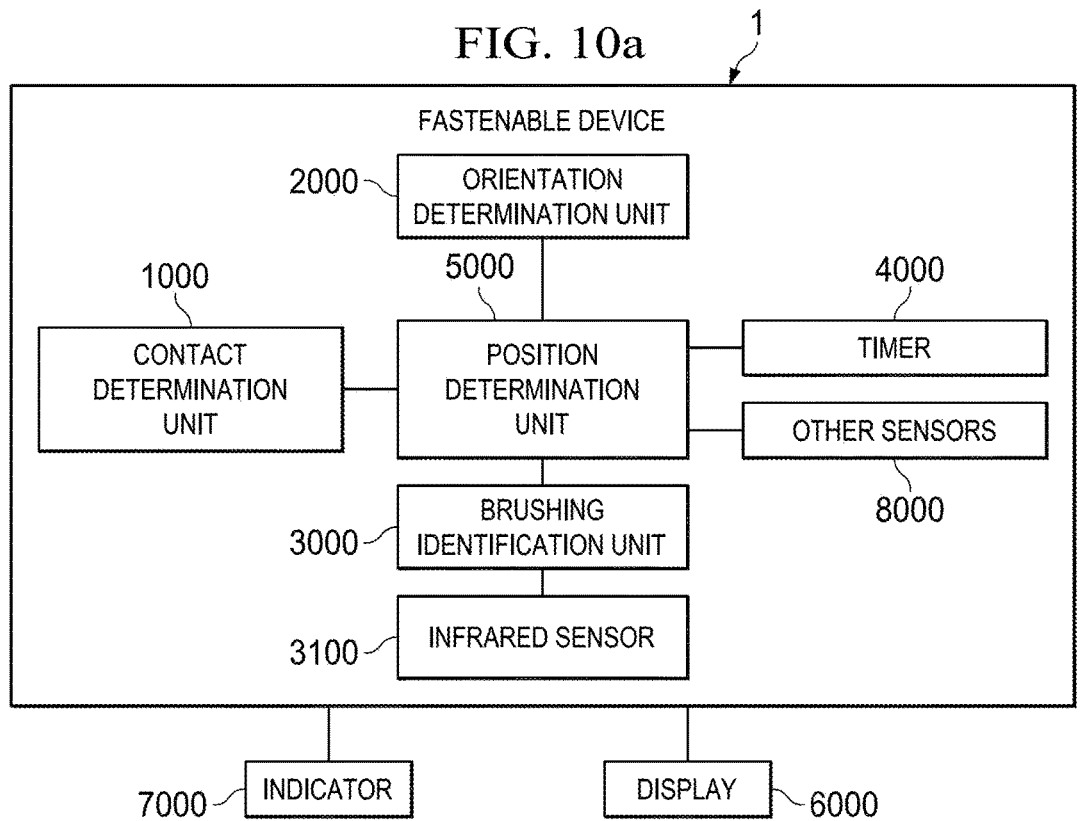
FIG. 10A is a block diagram illustrating a fastenable device comprising the electrical circuit for determining contact information according to the embodiment of FIG. 2-6.

Referring to FIG. 10A, the device (1) further comprises a position determination unit (5000). The position determination unit (5000) may be in communication with the contact determination unit (1000), for determining an oral cavity position, e.g., of the toothbrush (31) to which the device (1) is fastened, based on at least the determined contact information. As used herein, the term "contact information" relates to whether a given side (e.g., a bristles side, an opposing rear side, a first side (in between the bristle side and rear side), and an opposing second side) is contacting a defined oral area. Based on this information, an oral cavity position may be estimated (in a given point of time). For example, if the rear side of the toothbrush (i.e., side opposing the bristles) is contacting the cheek during brushing, it can be estimated that the oral cavity position of bristle head (39) is between the cheek and the teeth with the bristle (41) facing the teeth.

Referring to FIG. 10A, in order to detect the oral cavity position (i.e., providing more location details than contact information), fastenable device (1) may further comprises an orientation determination unit (2000) in communication with the position determination unit (5000). The orientation determination unit (2000) may be configured for obtaining orientation data of the fastenable device (1), and the position determination unit (5000) may be configured for determining the oral cavity position further based on the obtained orientation information. The orientation determination unit (2000) may be selected from the group consisting of a 3-axis accelerometer, a 3-axis gyroscope, a geomagnetic sensor, and combinations thereof. In an embodiment, referring to FIG. 7, a 3-axis (x, y, and z axes) accelerometer (not shown) is provided within the device housing (3), for example, attached to the PCB (not shown). The accelerometer may be installed (and ultimately so the fastenable device (1) is fastened to the toothbrush (31)) so that the x axis is parallel to the side of the bristles (41) and orthogonal to a lengthwise elongation axis L of the toothbrush (31), the y axis matches the lengthwise elongation axis L of the toothbrush (31), and the z axis is orthogonal to the side of the bristles (41). A gravity acceleration vector may be used to indicate the orientation of the toothbrush (31). For example, when the toothbrush (31) (with the device (1) fastened thereon) vertically stands on a horizontal table surface with the lengthwise elongation axis L of the toothbrush (31) orthogonal to the horizontal table surface, the gravity acceleration vector is parallel to the y axis. When the toothbrush (31) is placed horizontally with the lengthwise elongation axis L of the toothbrush (31) parallel to a horizontal plane, and with side of the bristles (41) pointing upward, the gravity acceleration vector is parallel to the z axis. When toothbrush (31) is placed horizontally with the lengthwise elongation axis L of the toothbrush (31) parallel to a horizontal plane, and with the side of the bristles (41) is pointed sideways, the gravity acceleration vector is parallel to the x axis.

In an embodiment, the 3-axis accelerometer comprises a micro electro mechanical system (MEMS). In a further embodiment, the accelerometer comprises a MEMS sensor selected from the group consisting of a piezoelectric resistance-type MEMS, an electrostatic capacitance-type MEMS, a thermal detection-type MEMS, and the combinations thereof. MEMS sensors are extremely small and can therefore easily be incorporated into the fastenable device (1) herein. Although not particularly shown, it is beneficial to provide correction circuits for correcting the balance of sensitivities, temperature characteristics of the sensitivities, temperature drift, and so on of the accelerometer in the respective axes. Furthermore, a band pass filter (low-pass filter) for removing dynamic acceleration components, noise, and so on may be provided. Further still, noise may be reduced by smoothing the waveforms of the outputs from the accelerometer. Other types of accelerometers may include an electrokinetic sensor, a strain gauge sensor, a piezoelectric sensor, or the like may be used.

Referring to FIG. 10A, the fastenable device (1) may further comprise an infrared sensor (3100) for sensing a temperature of bristles (41) or a defined oral area, and a brushing identification unit (3000), in communication with the infrared sensor (3100), for identifying contact information of the bristles with tooth or gum based on the sensed bristle temperature. The infrared sensor (3100) may be able to sense each bristle's temperature. Alternatively, the infrared sensor (3100) may be disposed on the housing (3) in such a way as to sense a temperature of an object facing the bristles (41) side. The object facing the bristles (41) side during tooth brushing may be tooth or gum. The brushing identification unit (3000) may be configured for identifying whether the bristles (41) side is facing tooth or gum based on the sensed temperature. The position determination unit (5000) may be in communication with the brushing identification unit (3000), and configured for determining the oral cavity position further based on the identified contact information of the bristles with tooth or gum. The infrared sensor (3100) may be, but is not limited to, a thermocouple or a thermopile.

The device (1) may further comprise a timer (4000). The timer (4000) may be configured for measuring a time duration at an oral cavity position. A display (6000) may be provided in communication with the device (1) or even on outside surface of the housing (3) viewable to the user (when the device is fastened to the oral care implement). The display (6000) may be configured for displaying the time duration at each oral cavity position. The display (6000) may be integrated into the device (1) or physically separate from the device (1). An indicator (7000) may also be provided in data communication with the device (1). The indicator (7000) may be configured for indicating whether the time duration is shorter or longer than a predetermined amount of time. The indicator (7000) may be integrated into the device (1) (e.g., housing (3)), or physically separate from the device (1), or even as a part of the display (6000).

Still referring to FIG. 10A, the device (1) may comprise a battery (not shown), housed in the housing (3), in electrical communication to the electrode memory, processor, or memory, or any other electrical component requiring power, preferably wherein the battery is rechargeable, more preferably wherein the battery is rechargeable wirelessly. The device (1) may comprise other sensors (8000a) including, but not limited, to biological sensors (e.g., assessing bacteria types and levels), tooth whitening, pH, temperature, diagnostic sensors (assessing oral conditions or disease), and the like. Data from these other sensors can be sent to the position determination unit (5000) and integrated with the other received data.

Figure 10B:
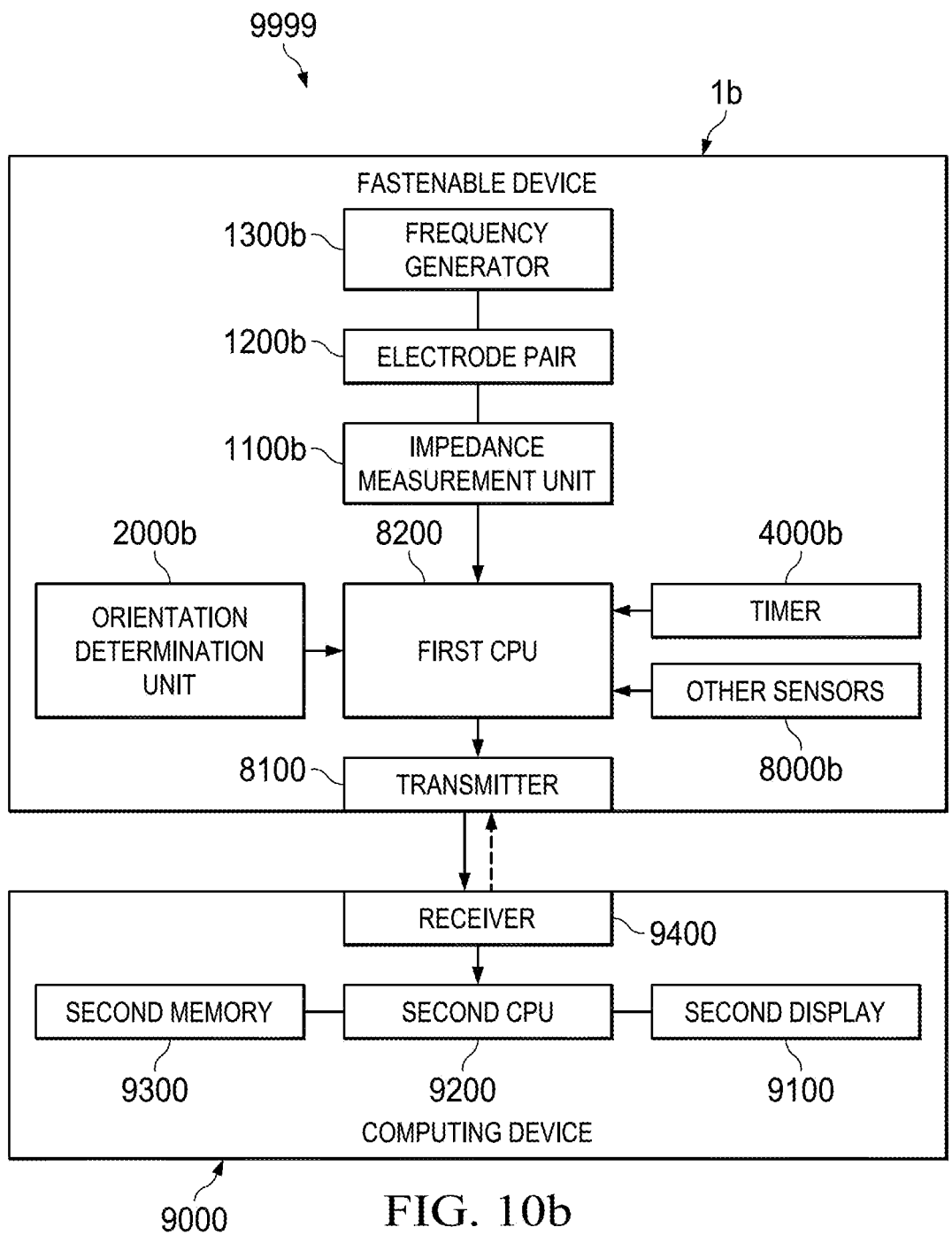
FIG. 10B is a block diagram illustrating a system with an alternative embodiment of the fastenable device and a computing device.

FIG. 10B describes another embodiment of the invention wherein a system (9999) is provided comprising the fastenable device (1b) and a computing device (9000). Non-limiting examples of a computing device (9000) include a smart phone or laptop computer or tablet computer or the like. There are several advantages of having a system (9999) as herein described. A first advantage is cost. One or more of the processing or memory functions is employed by the computing device (9000) versus the fastenable device (1b).

For example, data from the impedance measurement unit (1100*b*) (or contact determination unit (not shown)), or data from the orientation determination unit (2000*b*), timer (4000*b*), brushing identification unit (not shown), infrared sensors (not shown), or other sensors (8000*b*) can be sent directly to the computing device (9000) for data processing or computing or storage. There are several ways data can be sent from the fastenable device (1*b*) to the computing device (9000). One way is directly through a wire such as a USB port or IEEE 1394 (Firewire) port or the like. Another way is wirelessly through near field communications (such as Bluetooth™, IEEE 802.15.1) or Wi-FI or WiMAX or the like. Preferably the wireless communications are effective for ±2-5 meters. The communications can be by way of visible light, ultrasound, infrared light, radio frequency, and other communication technologies. Of course other wire-replacement communications hardware and software may be used, preferably with low power consumption.

A second advantage of the system (9999) is a more desirable user interface including web sites and convenience of software updates and a larger display that a computing device (9000) will typically have. A computing device (9000) may be able to track historical results or compare to standards or other personal objectives of the user's oral hygiene goals, and the like. Still referring to FIG. 10B, the fastenable device (1*b*) may have a first central processing unit or a first CPU (8200). The first CPU (8200) is preferably a lost cost one having relatively low computing power and power consumption. The first CPU (8200), in this alternative embodiment of the invention, is one that simply receives data received from one or more sensors or measuring units (e.g., 1200*b*, 1100*b*, 2000*b*, 4000*b*, 8000*b*) and sends the data to the transmitter (8100) for data transmission to the computing device (9000). The frequency generator (1300*b*), electrode pair(s) (1200*b*), and impedance measuring unit (1100*b*) are all in electrical communication with each other, and ultimately to the first CPU (8200). A frequency generator (1300*b*) is electrically connected to the electrode pair(s) (1200*b*), for applying a voltage with at least two different frequencies between the electrode pair(s) (1200*b*). An impedance measurement unit (1100*b*) is electrically coupled to the electrode pair (1200*b*), for measuring impedance values between the electrode pair at different frequencies. The measured impedance values are sent as data to the first CPU (8200) from the impedance measurement unit (1100*b*). The orientation determination unit (2000*b*), timer (4000*b*), and other sensors (8000*b*) collect data and are also in electrical communication with the first CPU (8200).

As illustrated in FIG. 10B the computing device (9000) receives data transmission from the fastenable device (1*b*) via a receiver (9400). The receiver (9400) may be in communication with the transmitter (8100) by wire or wirelessly as previously explained. Information or data can be also be sent from the computing device (9000) to the fastenable device (1*b*) such as software updates and the like. The second CPU (9200) is much more powerful than the aforementioned first CPU (8200). The second CPU (9200) is configured to have enough computational capacity to provide oral area position detection from the received data transmission. The oral area position detection information can be stored as computer readable memory in a second memory (9300). The second CPU (9200) is in communication with the second memory (9300). The second CPU (9200) is also in electrical communication to display the oral area position detection information on the second display (9100). Preferably the computing device (9000) comprises a web interface (not shown) configured to upload and download stored data or information to and from a remote server (e.g., web site). Of course the various components herein described are all electrically coupled to a power source (e.g., battery or wall socket) (not shown). The first and second CPUs (8200, 9200) may have software and algorithms providing processing instructions.

In one aspect the system (9999) comprises a fastenable device (1*b*) and a computing device (9000). The fastenable device (1*b*) comprises an electric pair (1200*b*) in electrical communication to an impedance measurement unit (1100*b*) providing impedance measurement data. Preferably the fastenable device (1*b*) further comprises an orientation determination unit (2000*b*) for providing orientation data, wherein more preferably the orientation determination unit (2000*b*) is an accelerometer (not shown) configured to provide accelerometer data. Lastly, the fastenable device (1*b*) further comprises a transmitter (8100), preferably a wireless transmitter (8100), configured to transmit the impedance measurement data and the optional accelerometer data.

The computing device (9000), preferably a portable computing device (9000), comprises a receiver (9400), preferably a wireless receiver (9400) configured to receive transmitted impedance measurement data and the optional accelerometer data (as well as optionally timer data and optionally other sensor data (as previously described). A second CPU (9200) is configured to process received data. A second memory (9300) is configured to store processed data. A second display (9100) is configured for displaying stored data or processed data. Lastly, the computing device (9000) may comprise a web interface (now shown) configured to inter alia upload stored or processed data to a remote server (not shown).

Contact Information Determination

During a tooth brushing cycle, the oral areas that may be contacted by a side (i.e., first side and opposing second side) of a toothbrush bristle head (39) mainly include a cheek area, a tongue area, and a saliva area, while bristles (41) disposed on the bristle head (39) (i.e., bristles (41) side) are contacting tooth and/or gum.

Referring back to FIGS. 7 and 8, five electrodes (13*a*, 13*b*, 13*c*, 13*d*, 13*e*) are provided on the head portion (9) of the device (1). These five electrodes essentially cover three out of four sides circumferentially around the L axis. These electrodes (13) constitute a plurality of electrode pairs (1200) which are used to determine whether each of the first side, the rear side and the second side of the toothbrush (31) is contacting a defined oral area or not.

During operation, each of the electrode pairs (1200) configured from the electrodes (13) (hereinafter collectively called as "the electrode pair 1200") is electrified with a voltage to form an impedance there between. Preferably the voltage may be provided by AC (alternating current) (for reasons explained below). Referring back to FIG. 9, at least two different frequencies are then applied by the frequency generator (1300) to the voltage between the electrified electrode pair (1200) Impedance values of the formed impedance between the electrified electrode pair (1200) are measured at the applied different frequencies by the impedance measurement unit (1100). The measurement of each electrode pair (1200) may be simultaneous or in sequence. A function is defined such that it correlates impedance values of the defined oral area at the applied different frequencies, and stored in the memory (1010) of the contact determination unit (1000). The measured impedance values are then processed to the stored function in the processor (1020) of the contact determination unit (1000). If the measured impedance values meet the stored function, a contact with the defined oral area will be determined.

The following discussion is based on the impedance magnitude variation of the cheek area, the tongue area, and the saliva area to further explain the contact information determination. As discussed hereinabove with regard to FIG. 1(a), the drop rate of the impedance magnitude in a frequency range from 10 kHz to 100 kHz is quite different between the cheek area, the tongue area, and the saliva area. What's even more advantageous is that the impedance magnitude of all these three areas drops almost linearly when the frequency increases in the range from 10 kHz to 100 kHz. This makes it possible to use a very simple linear function to differentiate these three defined oral areas from each other, which requires the impedance magnitudes at only two different frequencies, and therefore consumes very low computation power. However, the skilled person in the art can readily understand that other frequency ranges and other functions reflecting the impedance magnitude variation over three or more frequencies may also be used alternatively to achieve the present invention. The skilled person in the art can also readily understand that other impedance values such as impedance phase as shown in FIG. 1(b) may also be used alternatively or even additionally to determine contact information.

Referring to FIG. 1(a), the linear function, which can be used to differentiate the cheek area, the tongue area and the saliva area in the frequency range from 10 kHz to 100 kHz, may comprise a ratio of A1/A2, wherein A1 is a first impedance magnitude measured at a first frequency, and A2 is a second impedance magnitude measured at a second frequency. Two threshold constants can be used to set limitations for identifying the cheek area, the tongue area, and the saliva area. For example, in the case when the second frequency is greater than the first frequency, when A1/A2 is less than a first threshold constant a, it can be identified as the saliva area. When A1/A2 is no less than a second threshold constant b, it can be identified as the cheek area. When A1/A2 is less than the second threshold constant b but no less than the first threshold constant a, it can be identified as the tongue area.

The value of the threshold constants may be determined by experimentation. For example, the first threshold constant a may be from 1.2 to 1.4, since this value generally cannot be reached by a contact with the saliva area while a contact with the tongue area can easily exceed this value. The second threshold constant b may be from 1.7 to 2.1 in differentiating a contact with the tongue area and a contact with the saliva area.

One or more functions may be defined and stored in the memory (1010). Each of the one or more functions correlates impedance values of one defined oral area at the applied different frequencies. The processor (1020) may process the measured impedance values to each of the one or more functions one-by-one to find the function which the measured impedance values meet (if at all).

Figure 11:
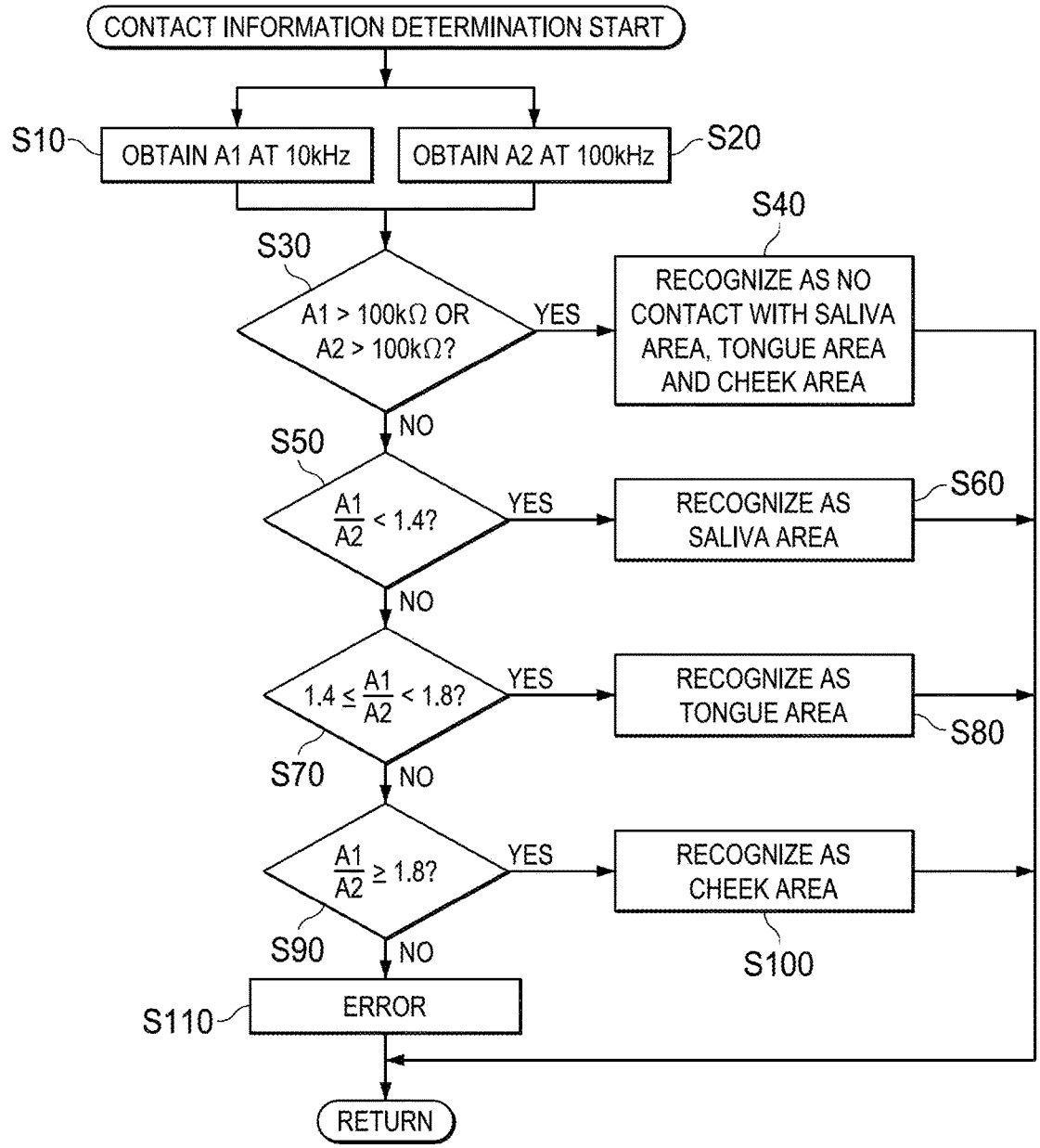
FIG. 11 shows a contact information determination process involving saliva area, tongue area and cheek area according to an embodiment of the present invention.

FIG. 11 shows an exemplary contact determination process to determine whether the bristles (41) side is contacting the defined oral area selected from the saliva area, the tongue area, and the cheek area. A side (e.g., bristles side, an opposing rear side; and first side (in between the bristle side and rear side), and opposing second side) has an electrode pair with a voltage to form an impedance there between. The applied different frequencies to the electrode pair comprise a first frequency (for example, 10 kHz) and a second frequency (for example, 100 kHz). A1 is a first impedance value (for example impedance magnitude) measured between the electrode pair at the first frequency (S10). A2 is a second impedance value (for example impedance magnitude) measured at the second frequency (S20) between the electrode pair. If any one of A1 and A2 is less than an impedance magnitude threshold (for example, 100 kΩ) ("YES" in S30), the side is recognized as not having contact with the saliva area, the tongue area or the cheek area (S40). The impedance magnitude threshold may be a value equal to or greater than the biggest impedance magnitude obtainable for the saliva area, the tongue area or the cheek area at the first and second frequencies. If neither A1 nor A2 is higher than the impedance magnitude threshold 100 kΩ ("NO" in S30), the side is contacting the saliva area, tongue area, or cheek area; and therefore the process proceeds to S50. If the ratio of A1/A2 is less than 1.4 (YES in S50), the side is contacting with saliva area (S60). If the answer to S50 is "NO," the process proceeds to S70. If the ratio of A1/A2 is equal to or greater than 1.4 but less than 1.8 (YES in S70), the side is contacting the tongue area (S80). If the answer to S70 is NO, the process proceeds to S90. If the ratio of A1/A2 is equal to or greater than 1.8 (YES in S90), the side is contacting the cheek area (S100). If the answer to S90 is NO, an error message is returned (S110). The error may be due to either of A1 and A2 or both equal to 0, which indicates there may be a short circuit or other dysfunctions. Note that rather than providing an error message as in S110, the processes of S10 to S90 may instead be repeated until contact information (including no contact and a contact with the saliva area, the tongue area, or the cheek area) is recognized. Note also that all the values shown in this exemplary contact determination process, including the frequency value, the impedance magnitude threshold value, and the ratio value, may be adjusted or changed to fit specific user(s).

The entire contact determination process may happen within 1 s, 500 ms, 50 ms, 10 ms, or 5 ms. The entire contact determination process may be automatically repeated every 1 s, 2 s, 3 s, 5 s, or 8 s during the teeth brushing action (or analogous oral care operation). The impedance values at the applied different frequencies are preferably measured within a time interval of less than 500 ms, 300 ms, 100 ms, 50 ms, 10 ms, 5 ms, or even 1 ms. This helps to confirm that the variation in the impedance values is due to the frequency change instead of a brush movement.

In practice, once the toothbrush bristle head (39) is inserted into the oral cavity and the user begins to brush, a saliva layer will surround the fastenable device's head portion (9) and the associated electrodes (13). When the head portion (9) is contacting the cheek or the tongue, a contact pressure is formed to make the saliva layer become very thin. This very thin saliva layer may significantly affect the impedance between the electrode pair in a direct current (DC) circuit so that the contact with the cheek or the tongue cannot be detected. However, in an AC circuit having voltage at varying frequencies, by selecting an appropriate frequency range in which the impedance of the cheek and/or the tongue changes much more significantly than that of the saliva, this very thin saliva layer can be ignored in detection of a contact with the cheek or the tongue. The present invention advantageously makes use of this finding, and provides an accurate contact information determination.

Oral Cavity Position Determination

Figure 12:
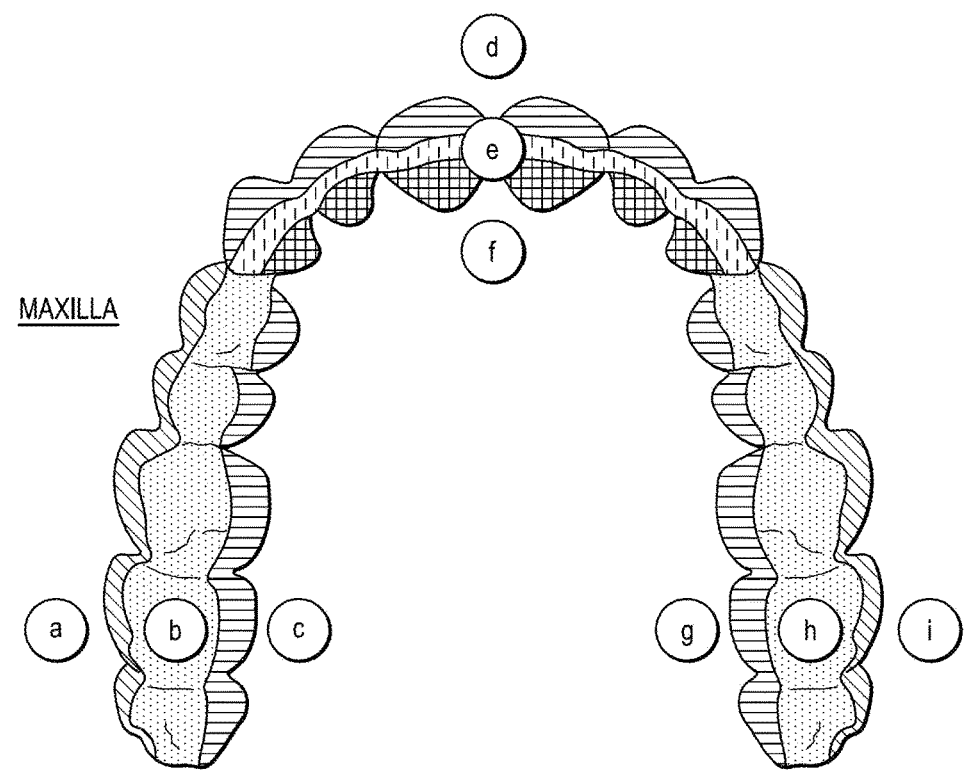
FIG. 12 is a diagram illustrating 18 tooth zones.
Figure 12:
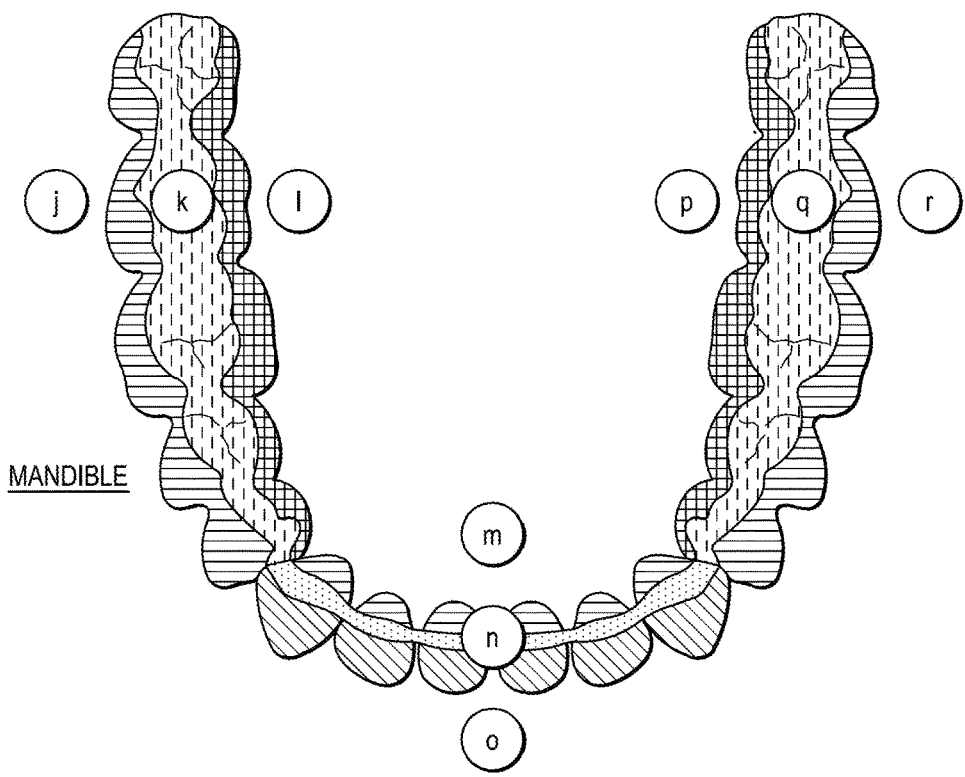
Figure 13A:
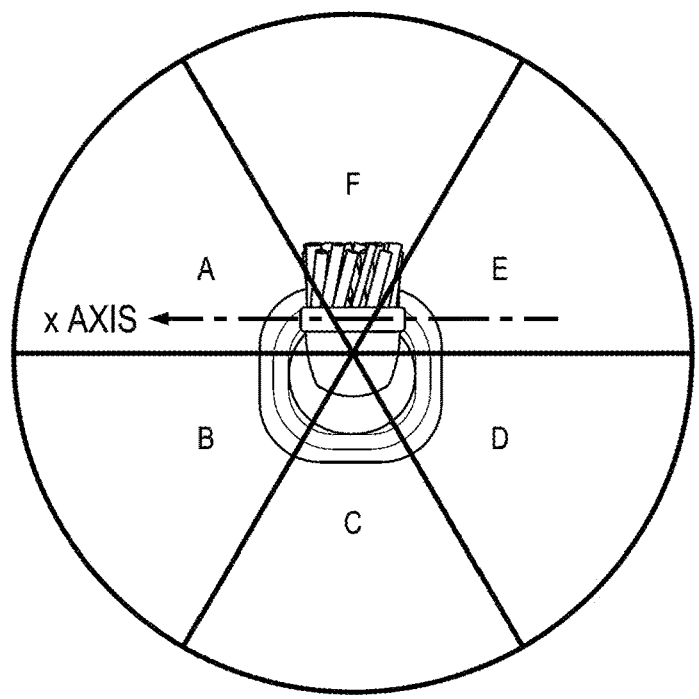
FIGS. 13A and 13B are diagrams illustrating 8 orientation sectors of a toothbrush during brushing.
Figure 13B:
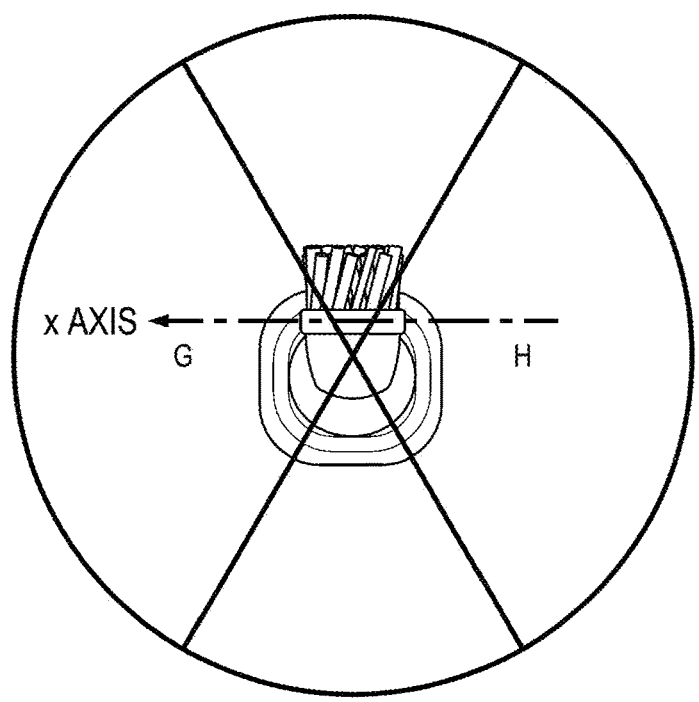

The oral cavity position of a toothbrush (with a fastenable device fastened thereon) may be defined by the bristle side facing a tooth zone. The tooth zone means an area or a region on a tooth or teeth. The number and location of the tooth zone may vary based on a specific purpose. In one example, 18 tooth zones are divided around a user's teeth, as shown in FIG. 12. These 18 tooth zones are distinguished from each other by each one's unique location inside the oral cavity. These tooth zones include: cheek side of upper left back teeth (zone a), occlusal side of upper left back teeth (zone b), tongue side of upper left back teeth (zone c), front side of upper front teeth (zone d), occlusal side of upper front teeth (zone e), tongue side of upper front teeth (zone f), tongue side of upper right back teeth (zone g), occlusal side of upper right back teeth (zone h), cheek side of upper right back teeth (zone i), cheek side of lower left back teeth (zone j), occlusal side of lower left back teeth (zone k), tongue side of lower left back teeth (zone l), tongue side of lower front teeth (zone m), occlusal side of lower front teeth (zone n), front side of lower front teeth (zone o), tongue side of lower right back teeth (zone p), occlusal side of lower right back teeth (zone q), and cheek side of lower right back teeth (zone r).

In an embodiment, the oral cavity position of the brush-head portion is determined based on the contact information of each side of the device head portion (and electrodes) with the cheek area, the tongue area or the saliva area. Table 1 shows hypothetical contact information of the rear side (opposing the bristle side), first side (in between the rear side and bristle side), and the second side opposing the first side, of the device (1) head portion (9) and disposed electrodes (13) (see e.g., FIGS. 7 and 8), wherein the bristles (41) side (esp. FIG. 7) is facing each tooth zone.

TABLE 1

Hypothetical contact information for each tooth zone

| Tooth zone faced by the bristle side 102 | Oral area contacted by the first side 106 | Oral area contacted by the rear side 104 | Oral area contacted by the second side 108 |
| --- | --- | --- | --- |
| a (cheek side of upper left back teeth) | cheek | cheek | saliva |
| b (occlusal side of upper left back teeth) | cheek | tongue | saliva |
| c (tongue side of upper left back teeth) | tongue | saliva | saliva |
| d (front side of upper front teeth) | No contact or saliva | No contact or saliva | No contact or saliva |
| e (occlusal side of upper front teeth) | No contact or saliva | No contact or saliva | No contact or saliva |
| f (tongue side of upper front teeth) | No contact or saliva | No contact or saliva | No contact or saliva |
| g (tongue side of upper right back teeth) | saliva | saliva | tongue |
| h (occlusal side of upper right back teeth) | saliva | tongue | cheek |
| i (cheek side of upper right back teeth) | saliva | cheek | cheek |
| j (cheek side of lower left back teeth) | saliva | cheek | cheek |
| k (occlusal side of lower left back teeth) | saliva | saliva | cheek |
| l (tongue side of lower left back teeth) | tongue | saliva | saliva |
| m (tongue side of lower front teeth) | No contact or saliva | No contact or saliva | No contact or saliva |
| n (occlusal side of lower front teeth) | No contact or saliva | No contact or saliva | No contact or saliva |
| o (front side of lower front teeth) | No contact or saliva | No contact or saliva | No contact or saliva |
| p (tongue side of lower right back teeth) | saliva | saliva | tongue |
| q (occlusal side of lower right back teeth) | cheek | saliva | saliva |
| r (cheek side of lower right back teeth) | cheek | cheek | saliva |

Based on the hypothetical contact information as shown in Table 1, there are some tooth zones having same contact information, for example zone a and zone r, which therefore cannot be identified from each other based on the contact information only. Furthermore, zones d, e, f, m, n, and o cannot be identified from each other because there is no contact with the cheek or the tongue.

Therefore, in a further embodiment, the oral cavity position of the bristle side is determined by combining the contact information with orientation information of the fastenable device. The orientation information may comprise an orientation angle formed between the bristle side and a horizontal plane. With a 3-axis (x, y, and z axes) accelerometer installed within the device (1), the x axis of the accelerometer is parallel to the bristle side and orthogonal to a lengthwise elongation axis L of the toothbrush, so the angle formed between the x axis of the accelerometer and a horizontal plane may be taken as the orientation angle. See e.g., FIG. 7.

For convenience, the brush orientation, defined by the orientation angle, may be broken down into 8 orientation sectors A to H as shown in FIG. 12. Each of the sectors A to F is 60 degrees large. Sector G is a combination of sectors A and B. Sector H is a combination of sectors D and E. These 8 orientation sectors correspond to 8 typical brush orientations when the 18 tooth zones as shown in FIG. 12 are brushed during a tooth brushing episode. For example, sector A corresponds to a brush orientation when the tongue side of upper left back teeth (zone c) is brushed, while sector B corresponds to a brush orientation when the tongue side of lower left back teeth (zone l) is brushed. The orientation angle at sector A is about 60°. The orientation angle at sector B is about 120°. Table 2 shows the orientation angle of the toothbrush and the tooth zone which might be brushed at each orientation sector.

TABLE 2

Orientation angle and tooth zone at each orientation sector

| Orientation sector | Orientation angle | Tooth zone which might be brushed |
| --- | --- | --- |
| A | 60° | c (tongue side of upper left back teeth) |
| B | 120° | l (tongue side of lower left back teeth) |
| C | 180° | k (occlusal side of lower left back teeth) |
|  |  | m (tongue side of lower front teeth) |
|  |  | n (occlusal side of lower front teeth) |
|  |  | q (occlusal side of lower right back teeth) |
| D | 240° | p (tongue side of lower right back teeth) |
| E | 300° | g (tongue side of upper right back teeth) |
| F | 360° | b (occlusal side of upper left back teeth) |
|  |  | e (occlusal side of upper front teeth) |
|  |  | f (tongue side of upper front teeth) |
|  |  | h (occlusal side of upper right back teeth) |
| G | 90° | d (front side of upper front teeth) |
|  |  | i (cheek side of upper right back teeth) |
|  |  | o (front side of lower front teeth) |
|  |  | r (cheek side of lower right back teeth) |
| H | 270° | a (cheek side of upper left back teeth) |
|  |  | d (front side of upper front teeth) |
|  |  | j (cheek side of lower left back teeth) |
|  |  | o (front side of lower front teeth) |

Table 3 shows how each of the 18 tooth zones as shown in FIG. 12 is identified by the combination of the contact information and the orientation information. The previously brushed tooth zone is taken into consideration to identify the tooth zones relating to the front teeth where no contact information with the cheek or the tongue is obtained. This is based on an assumption that the user generally brushes teeth from one zone to another adjacent zone. An algorithm represented by Table 3 may be programmed into the position determination unit (5000) (FIG. 10) to distinguish all 18 tooth zones from each other.

TABLE 3

Tooth zone identification by combining contact information and orientation information.

| Tooth zone to be identified | Contact information | | | Orientation sector | Previously brushed tooth zone |
|---|---|---|---|---|---|
| | Oral area contacted by the first side | Oral area contacted by the rear side | Oral area contacted by the second side | | |
| a (cheek side of upper left back teeth) | cheek | cheek | saliva | H | — |
| b (occlusal side of upper left back teeth) | cheek | tongue | saliva | F | — |
| c (tongue side of upper left back teeth) | tongue | saliva | saliva | A | — |
| d (front side of upper front teeth) | No contact or saliva | No contact or saliva | No contact or saliva | G or H | a or i |
| e (occlusal side of upper front teeth) | No contact or saliva | No contact or saliva | No contact or saliva | F | b or h |
| f (tongue side of upper front teeth) | No contact or saliva | No contact or saliva | No contact or saliva | F | c or g |
| g (tongue side of upper right back teeth) | saliva | saliva | tongue | E | — |
| h (occlusal side of upper right back teeth) | saliva | tongue | cheek | F | — |
| i (cheek side of upper right back teeth) | saliva | cheek | cheek | G | — |
| j (cheek side of lower left back teeth) | saliva | cheek | cheek | H | — |
| k (occlusal side of lower left back teeth) | saliva | saliva | cheek | C | — |
| l (tongue side of lower left back teeth) | tongue | saliva | saliva | B | — |
| m (tongue side of lower front teeth) | No contact or saliva | No contact or saliva | No contact or saliva | C | l or p |
| n (occlusal side of lower front teeth) | No contact or saliva | No contact or saliva | No contact or saliva | C | k or q |
| o (front side of lower front teeth) | No contact or saliva | No contact or saliva | No contact or saliva | G or H | j or r |
| p (tongue side of lower right back teeth) | saliva | saliva | tongue | D | — |
| q (occlusal side of lower right back teeth) | cheek | saliva | saliva | C | — |
| r (cheek side of lower right back teeth) | cheek | cheek | saliva | G | — |

Therefore, all the 18 tooth zones are distinguished by the present invention in a non-intrusive, precise and accurate way at low cost. According to the present invention, the user doesn't have to wear any equipment which may be considered as being intrusive. Head movements and walking around while brushing do not disturb the position detection of the present invention as it is the case with the systems which use accelerometer only, so that good precision and accuracy are provided. The contact determination relies on electrode pairs which can be easily injected as a conductive paste in the toothbrush in mass production, which is favorably cost-effective. The device also provides the convenience of being removable from the toothbrush when bristles need to be replaced etc., and thereby saving the costs of electronics.

In an even further embodiment, the oral cavity position of the bristle side is further determined by a tooth/gum brushing identification process. There is a temperature difference between tooth and gum. Temperature is higher in the gum where there is blood compared to tooth where there is no blood. Referring back to FIG. 10, a temperature can be obtained by an infrared sensor (3100) during brushing. The temperature may be a bristle temperature or a temperature of a target (e.g., oral care tissue). If the temperature is greater than or equal to a first threshold (for example, 34.5° C.), it is determined that gum is being brushed. If the bristle temperature is less than the first threshold but greater than or equal to a second threshold (for example, 31° C.), it is determined that a tooth is being brushed. This tooth/gum brushing identification information is especially advantageous when the brushing time for each tooth zone is recorded as a feedback. By this brushing identification process, the gum brushing time and teeth brushing time may be separately recorded so that the user can get a more precise and more accurate brushing feedback.

As shown in FIG. 10, the display (6000) and the indicator (7000) may be provided as a user interface, for displaying and indicating information associated with the oral cavity position, so that the user may improve the brushing quality by optimizing their brushing procedure based on this information. The display and/or indicator may be integral to the device (i.e., viewable on the device) or may be external to the device.

In an embodiment, the display (6000) comprises a diagram illustrating 18 tooth zones as shown in FIG. 12. A real-time feedback may be provided by lightening the tooth zone which has been brushed or is being brushed during brushing. Another real-time feedback may be provided by showing green if the tooth zone has received enough brushing and showing red if not enough brushing. Additionally, the tooth zone may blink if there is too much brushing. A summary feedback may be provided by showing how much time is used for each tooth zone during and/or after the brushing. An overall brushing result may be provided by showing if any tooth zone was missed or if all the tooth zones have been brushed properly. Such feedback would motivate the user to re-brush the tooth zones which have been missed or not brushed with enough time. The display can be an LED display viewable on the housing of the device. Alternatively, the display may be in on a computing device (9000) as in FIG. 10B.

In an embodiment, the indicator (7000) provides a visual, audio and/or physical signal to indicate the user to change the brushing tooth zone when the time used for one tooth zone is longer than a predetermined amount of time. The signals may be embodied on the device or on the display 6000. For example, a physical signal may comprise the vibration of the device (and therefore the toothbrush).

In an embodiment, the indicator (7000) provides a visual, audio and/or physical signal to indicate the user to deliver a specific active such as a whitening active on the tooth surface when a certain tooth zone is reached.

More information associated with the oral cavity position may be provided by a user interface to benefit the user, such as those disclosed in WO2008060482A2, paragraphs 24 to 26 of WO201177282A1, and columns 15 to 16 of U.S. Pat. No. 8,479,341B2. All the information may be displayed or indicated simultaneously or in sequence. The user may have a control on the information to be displayed or indicated. The display (6000) or indicator (7000) can be in electrical communication to the processor (1020).

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A fastenable device comprising:
    a housing comprising a base portion, a head portion opposite to the base portion, and a body portion between the base portion and the head portion, wherein the base portion comprises a first fastener in the form of a full ring integral to the housing and defining a through-hole, and wherein the head portion comprises a second fastener in the form of an open ring integral to the housing and defining a snappable recess;
    a frequency generator housed in the housing and electrically connected to an electrode pair disposed on the housing, for applying a voltage with at least two different frequencies between the electrodes;
    an accelerometer providing accelerometer data;
    an impedance-measure unit in communication with the electrode pair and providing impedance-measurement data; and
    a wireless transmitter in communication with the accelerometer and the impedance measure unit.

2. The device of claim 1, further comprising an electrical source electrically connecting to the electrode pair to form an impedance between the electrodes when electrified.

3. The device of claim 2, wherein the head portion comprises a plurality of electrodes disposed thereon configured to form an impedance therebetween when electrified.

4. The device of claim 3, wherein the plurality of electrodes comprises at least four electrode pairs.

5. The device of claim 1, wherein the head portion comprises a plurality of electrodes disposed thereon and configured to form an impedance therebetween when electrified.

6. The device of claim 5, wherein the plurality of electrodes comprises at least four electrode pairs.

7. A method of fastening a fastenable device to a toothbrush neck, comprising the steps:
    (a) providing the fastenable device according to claim 1;
    (b) providing a toothbrush comprising a handle portion and an opposing bristle head, with the neck portion being disposed between the handle portion and the bristle portion;
    (c) sliding the bristle head through the through-hole of the first fastener until the handle portion abuts the first fastener; and
    (d) squeezing the head portion or the body portion and the toothbrush neck portion together until the snappable recess snaps around at least a portion of the toothbrush neck thereby fastening the fastenable device to the toothbrush neck.

8. A fastenable device comprising:
    a housing comprising a base portion, an opposing head portion, and a body portion therebetween, wherein the base portion includes a first fastener comprising a first open ring integral to the housing and defining a first snappable recess, wherein the head portion includes a second fastener comprising a second open ring integral to the housing and defining a second snappable recess;
    a frequency generator housed in the housing and electrically connected to an electrode pair disposed on the housing for applying a voltage with at least two different frequencies between the electrodes;
    an accelerometer providing accelerometer data;
    an impedance-measure unit in communication with the electrode pair and providing impedance-measurement data; and
    a wireless transmitter in communication with the accelerometer and the impedance-measure unit.

9. The device of claim 8, further comprising an electrical source electrically connecting to the electrode pair to form an impedance between the electrodes when electrified.

10. The device of claim 9, wherein the head portion comprises a plurality of electrodes disposed thereon and configured to form an impedance therebetween when electrified.

11. The device of claim 10, wherein the plurality of electrodes comprise at least four electrode pairs.

12. The device of claim 8, wherein the head portion comprises a plurality of electrodes disposed thereon and configured to form an impedance therebetween when electrified.

13. The device of claim 12, wherein the plurality of electrodes comprises at least four electrode pairs.

* * * * *